US010066217B2

(12) United States Patent
Shaw, IV et al.

(10) Patent No.: US 10,066,217 B2
(45) Date of Patent: Sep. 4, 2018

(54) THERMOPHILIC ORGANISMS FOR CONVERSION OF LIGNOCELLULOSIC BIOMASS TO ETHANOL

(75) Inventors: Arthur Josephus Shaw, IV, West Lebanon, NH (US); Sunil G. Desai, Ellicott City, MA (US); Lee R. Lynd, Meriden, NH (US); Kara Podkaminer, Hanover, NH (US); John Bardsley, Cambridge, MA (US); David Anthony Hogsett, Grantham, NH (US)

(73) Assignee: THE TRUSTEES OF DARTMOUTH COLLEGE, Hanover, NH (US)

(*) Notice: Subject to any disclaimer, the term of this patent is extended or adjusted under 35 U.S.C. 154(b) by 74 days.

(21) Appl. No.: 12/299,070

(22) PCT Filed: May 1, 2007

(86) PCT No.: PCT/US2007/067941
§ 371 (c)(1),
(2), (4) Date: Apr. 24, 2009

(87) PCT Pub. No.: WO2007/130984
PCT Pub. Date: Nov. 15, 2007

(65) Prior Publication Data
US 2009/0221049 A1 Sep. 3, 2009
US 2012/0077239 A9 Mar. 29, 2012

(51) Int. Cl.
*C12N 9/10* (2006.01)
*C12N 9/88* (2006.01)
*C12N 9/12* (2006.01)
*C12P 7/04* (2006.01)
*C12P 7/16* (2006.01)
*C12N 9/04* (2006.01)
*C12P 7/10* (2006.01)
*C12R 1/145* (2006.01)

(52) U.S. Cl.
CPC ......... *C12N 9/1029* (2013.01); *C12N 9/0006* (2013.01); *C12N 9/1217* (2013.01); *C12P 7/10* (2013.01); *C12R 1/145* (2013.01); *C12Y 203/01008* (2013.01); *C12Y 207/02001* (2013.01); *Y02E 50/16* (2013.01); *Y02E 50/17* (2013.01)

(58) Field of Classification Search
CPC .... C12N 9/006; C12N 9/1029; C12N 9/1217; C12P 7/10
USPC .......................... 435/320.1, 252.3, 161, 189
See application file for complete search history.

(56) References Cited

U.S. PATENT DOCUMENTS 5,182,199 A * 1/1993 Hartley .......................... 435/162
2004/0146996 A1* 7/2004 Yocum et al. ................. 435/106

FOREIGN PATENT DOCUMENTS

WO    WO 2005/118828 A    12/2005

OTHER PUBLICATIONS

Desai et al, Appld. Micriobiol and Biotechnol 2004, vol. 65, pp. 600-605.*
Furdui et al. JBC 2000, 275, pp. 28494-28499.*
Office Action dated Jul. 8, 2011, issued in related U.S. Appl. No. 12/298,876, 24 pages.
Office Action dated Jan. 15, 2016 in Malaysian Patent Application No. PI 20081364, 5 pp.
Mayer, et al., "Isolation and Properties of Acetate Kinase-and Phosphotransacetylase-Negative Mutants of Thermoanaerobacter Thermohydrosulfuricus," Microbiology, vol. 141, pp. 2891-2896, 1995.
Desai, S.G., et al., "Cloning of L-lactate Dehydrogenase and Elimination of Lactic Acid Production via Gene Knockout in Thermoanaerobacterium Saccharolyticum JW/SL-YS485" Applied Microbiology and Biotechnology, Springer Verlag, Berlin, Germany vol. 65, No. 5, Mar. 6, 2004, pp. 600-605.
Lynd, L.R., et al. "Microbial Cellulose Utilization: Fundamentals and Biotechnology" Microbiology and Molecular Biology Reviews, American Society for Microbiology, US, vol. 66, No. 3, Sep. 2002, pp. 506-577.
Payton, M.A., "Production of Ethanol by Thermophilic Bacteria" Trends in Biotechnology, Elsevier, Amsterdam, Netherlands, vol. 2, No. 6, 1984, pp. 153-158.
Biswas, I, et al., "High-Efficiency Gene Inactivation and Replacement System for Gram-Positive Bacteria" Journal of Bacteriology, Washing D.C., US, vol. 175, No. 11, Jun. 1, 1993, pp. 3628-3635.
Sun, Y., et al. "Hydrolysis of Lingnocellulosic Materials for Ethanol Production: A Review," Bioresource Technology, Elsevier, Great Britain, vol. 83, 2002, pp. 1-11.

(Continued)

*Primary Examiner* — Tekchand Saidha
*Assistant Examiner* — Mohammad Y Meah
(74) *Attorney, Agent, or Firm* — Lathrop Gage LLP

(57) ABSTRACT

Mutant thermophilic organisms that consume a variety of biomass derived substrates are disclosed herein. Strains of *Thermoanaerobacterium saccharolyticum* with acetate kinase and phosphotransacetylase expression eliminated are disclosed herein. Further, strain ALK1 has been engineered by site directed homologous recombination to knockout both acetic acid and lactic acid production. Continuous culture involving a substrate concentration challenge lead to evolution of ALK1, and formation of a more robust strain designated ALK2. The organisms may be utilized for example in thermophilic SSF and SSCF reactions performed at temperatures that are optimal for cellulase activity to produce near theoretical ethanol yields without expressing pyruvate decarboxylase.

20 Claims, 17 Drawing Sheets

Specification includes a Sequence Listing.

(56) References Cited

OTHER PUBLICATIONS

Lin, Y., et al. "Ethanol Fermentation From Biomass Resources: Current State and Prospects" Applied Microbiology and Biotechnology, Springer Verlag, Berlin, Germany, vol. 69, No. 6,k Dec. 6, 2005, pp. 627-642.
Hahn-Hagerdal, et al., "Bio-Ethanol the Fuel of Tomorrow From the Residues of Today" Trends in Biotechnology, Elsevier Publications, Cambridge, Gret Britain, vol. 24, No. 12, Nov. 18, 2006, pp. 549-556.
International Search Report and Written Opinion issued in related PCT Patent Application Serial No. PCT/US07/67941, dated May 2, 2008, 19 pages.
International Search Report and Written Opinion issued in related PCT Patent Application Serial No. PCT/US07/42442, dated Apr. 11, 2007, 12 pages.
Office Action dated Aug. 13, 2009 in related European Patent Application 07783037.0, 4 pages.
Office Action dated Jul. 23, 2009 in related European Patent Application 06844238.3, 5 pages.

\* cited by examiner

1. Lactate dehydrogenase
2. Pyruvate-ferredoxin oxidoreductase
3. NADH-ferredoxin oxidoreductase
4. Hydrogenase
5. Phosphotransacetylase
6. Acetate kinase
7. Acetaldehyde dehydrogenase
8. Alcohol dehydrogenase
9. Pyruvate decarboxylase (NOT PRESENT)

Fig. 3A

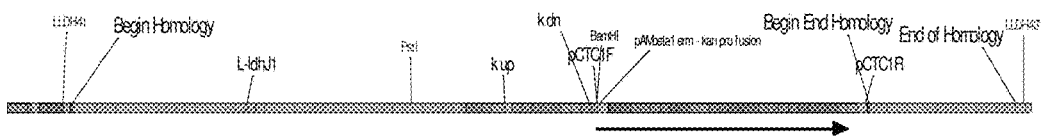

**Sequence alignment – *L-ldh* locus**

```
Line 1: Compiled sequence from ALK1 strain (SEQ ID NO: 9)
Line 2: Expected sequence based on L-ldh sequence and suicide vector pSGD8-
erm Consensus key
* - single, fully conserved residue
  - no consensus CLUSTAL W (1.81) multiple sequence alignment lldh_erm_CAP3_seq_compiled     ------------------------------------GGAAACGAATAG
L-ldh_erm_region               CGATAAAGAACATGGCTGGATAANTACTATAACTCCAAGGAAACGAATAG
                                                                   ************** lldh_erm_CAP3_seq_compiled     TAAAGGAATGGAGGCGAATTAATGAGTAATGTCGCAATGCAATTAATAGA
L-ldh_erm_region               TAAAGGAATGGAGGCGAATTAATGAGTAATGTCGCAATGCAATTAATAGA
                               ************************************************** lldh_erm_CAP3_seq_compiled     AATTTGTCGGAAATATGTAAATAATAATTTAAACATAAATGAATTTATCG
L-ldh_erm_region               AATTTGTCGGAAATATGTAAATAATAATTTAAACATAAATGAATTTATCG
                               ************************************************** lldh_erm_CAP3_seq_compiled     AAGACTTTCAAGTGCTTTATGAACAAAAGCAAGATTTATTGACAGATGAA
L-ldh_erm_region               AAGACTTTCAAGTGCTTTATGAACAAAAGCAAGATTTATTGACAGATGAA
                               ************************************************** lldh_erm_CAP3_seq_compiled     GAAATGAGCTTGTTTGATGATATTTATATGGCTTGTGAATACTATGAACA
L-ldh_erm_region               GAAATGAGCTTGTTTGATGATATTTATATGGCTTGTGAATACTATGAACA
                               ************************************************** lldh_erm_CAP3_seq_compiled     GGATGAAAATATAAGAAATGAATATCACTTGTATATTGGAGAAAATGAAT
L-ldh_erm_region               GGATGAAAATATAAGAAATGAATATCACTTGTATATTGGAGAAAATGAAT
                               ************************************************** lldh_erm_CAP3_seq_compiled     TAAGACAAAAAGTGCAAAAACTTGTAAAAAAGTTAGCAGCATAATAAACC
L-ldh_erm_region               TAAGACAAAAAGTGCAAAAACTTGTAAAAAAGTTAGCAGCATAATAAACC
                               ************************************************** lldh_erm_CAP3_seq_compiled     GCTAAGGCATGATAGCTAAAGCGGTATTTTTATGCAATTAAAAGGATGAA
L-ldh_erm_region               GCTAAGGCATGATAGCTAAAGCGGTATTTTTATGCAATTAAAAGGATGAA
                               **************************************************
```

```
lldh_erm_CAP3_seq_compiled    ATGATATCTGATAAACTGCGAAAAAGTATTTTAGAAAATAACTATAAAGA
L-ldh_erm_region              ATGATATCTGATAAACTGCGAAAAAGTATTTTAGAAAATAACTATAAAGA
                              ************************************************** lldh_erm_CAP3_seq_compiled    TAATATTTCAAATCAATAAGGACAAAATAAGATTAAAATTTAGACAATTT
L-ldh_erm_region              TAATATTTCAAATCAATAAGGACAAAATAAGATTAAAATTTAGACAATTT
                              ************************************************** lldh_erm_CAP3_seq_compiled    CATCAAAACTATGTTATAATATTATTAAAGGAAAATACATATTATTTAGG
L-ldh_erm_region              CATCAAAACTATGTTATAATATTATTAAAGGAAAATACATATTATTTAGG
                              ************************************************** lldh_erm_CAP3_seq_compiled    AGGCGATGTAATGAGCAAGGTAGCAATAATAGGATCTGGTTTTGTAGGTG
L-ldh_erm_region              AGGCGATGTAATGAGCAAGGTAGCAATAATAGGATCTGGTTTTGTAGGTG
                              ************************************************** lldh_erm_CAP3_seq_compiled    CAACATCGGCATTTACGCTGGCATTAAGTGGGACTGTGACAGATATCGTG
L-ldh_erm_region              CAACATCGGCATTTACGCTGGCATTAAGTGGGACTGTGACAGATATCGTG
                              ************************************************** lldh_erm_CAP3_seq_compiled    CTGGTGGATTTAAACAAGGACAAGGCTATAGGCGATGCACTGGACATAAG
L-ldh_erm_region              CTGGTGGATTTAAACAAGGACAAGGCTATAGGCGATGCACTGGACATAAG
                              ************************************************** lldh_erm_CAP3_seq_compiled    CCATGGCATACCGCTAATACAGCCTGTAAATGTGTATGCAGGTGACTACA
L-ldh_erm_region              CCATGGCATACTGCTAATACAGCCTGTAAATGTGTATGCAGGTGACTACA
                              ********* ************************************ lldh_erm_CAP3_seq_compiled    AAGATGTGAAAGGCGCAGATGTAATAGTTGTGACAGCAGGTGCTGCTCAA
L-ldh_erm_region              AAGATGTGAAAGGCGCAGATGTAATAGTTGTGACAGCAGGTGCTGCTCAA
                              ************************************************** lldh_erm_CAP3_seq_compiled    AAGCCGGGAGAGACACGGCTTGACCTTGTAAAGAAAAATACAGCCATATT
L-ldh_erm_region              AAGCCGGGAGAGACACGGCTTGACCTTGTAAAGAAAAATACAGCCATATT
                              ************************************************** lldh_erm_CAP3_seq_compiled    TAAGTCCATGATACCTGAGCTTTTAAAGTACAATGACAAGGCCATATATT
L-ldh_erm_region              TAAGTCCATGATACCTGAGCTTTTAAAGTACAATGACAAGGCCATATATT
                              ************************************************** lldh_erm_CAP3_seq_compiled    TGATTGTGACAAATCCCGTAGATATACTGACGTACGTTACATACAAGATT
L-ldh_erm_region              TGATTGTGACAAATCCCGTAGATATACTGACGTACGTTACATACAAGATT
                              ************************************************** lldh_erm_CAP3_seq_compiled    TCTGGACTTCCATGGGGCAGAGTTTTTGGTTCTGGCACCGTTCTTGACAG
L-ldh_erm_region              TCTGGACTTCCATGGGGCAGAGTTTTTGGTTCTGGCACCGTTCTTGACAG
                              ************************************************** lldh_erm_CAP3_seq_compiled    CTCAAGGTTTAGATACCTTTTAAGCAAGGACTGCTGCAGGTCGATAAACC
L-ldh_erm_region              CTCAAGGTTTAGATACCTTTTAAGCAAGGACTGCTGCAGGTCGATAAACC
                              ************************************************** lldh_erm_CAP3_seq_compiled    CAGCGAACCATTTGAGGTGATAGGTAAGATTATACCGAGGTATGAAAACG
L-ldh_erm_region              CAGCGAACCATTTGAGGTGATAGGTAAGATTATACCGAGGTATGAAAACG
                              **************************************************
```

*Fig. 3B*

| | |
|---|---|
| lldh_erm_CAP3_seq_compiled | AGAATTGGACCTTTACAGAATTACTCTATGAAGCGCCATATTTAAAAAGC |
| L-ldh_erm_region | AGAATTGGACCTTTACAGAATTACTCTATGAAGCGCCATATTTAAAAAGC |
| | ************************************************** |
| lldh_erm_CAP3_seq_compiled | TACCAAGACGAAGAGGATGAAGAGGATGAGGAGGCAGATTGCCTTGAATA |
| L-ldh_erm_region | TACCAAGACGAAGAGGATGAAGAGGATGAGGAGGCAGATTGCCTTGAATA |
| | ************************************************** |
| lldh_erm_CAP3_seq_compiled | TATTGACAATACTGATAAGATAATATATCTTTTATATAGAAGATATCGCC |
| L-ldh_erm_region | TATTGACAATACTGATAAGATAATATATCTTTTATATAGAAGATATCGCC |
| | ************************************************** |
| lldh_erm_CAP3_seq_compiled | GTATGTAAGGATTTCAGGGGGCAAGGCATAGGCAGCGCGCTTATCAATAT |
| L-ldh_erm_region | GTATGTAAGGATTTCAGGGGGCAAGGCATAGGCAGCGCGCTTATCAATAT |
| | ************************************************** |
| lldh_erm_CAP3_seq_compiled | ATCTATAGAATGGGCAAAGCATAAAAACTTGCATGGACTAATGCTTGAAA |
| L-ldh_erm_region | ATCTATAGAATGGGCAAAGCATAAAAACTTGCATGGACTAATGCTTGAAA |
| | ************************************************** |
| lldh_erm_CAP3_seq_compiled | CCCAGGACAATAACCTTATAGCTTGTAAATTCTATCATAATTGTGGTTTC |
| L-ldh_erm_region | CCCAGGACAATAACCTTATAGCTTGTAAATTCTATCATAATTGTGGTTTC |
| | ************************************************** |
| lldh_erm_CAP3_seq_compiled | AAAATCGGCTCCGTCGATACTATGTTATACGCCAACTTTGAAAACAACTT |
| L-ldh_erm_region | AAAATCGGCTCCGTCGATACTATGTTATACGCCAACTTTCAAAACAACTT |
| | **************************************** ********* |
| lldh_erm_CAP3_seq_compiled | TGAAAAGCTGTTTTCTGGTATTTAAGGTTTTAGAATGCAAGGAACAGTG |
| L-ldh_erm_region | TGAAAAGCTGTTTTCTGGTATTTAAGGTTTTAGAATGCAAGGAACAGTG |
| | ************************************************** |
| lldh_erm_CAP3_seq_compiled | AATTGGAGTTCGTCTTGTTATAATTAGCTTCTTGGGGTATCTTTAAATAC |
| L-ldh_erm_region | AATTGGAGTTCGTCTTGTTATAATTAGCTTCTTGGGGTATCTTTAAATAC |
| | ************************************************** |
| lldh_erm_CAP3_seq_compiled | TGTAGAAAAGAGGAAGGAAATAATAAATGGCGGATCCCATGAACAAAAAT |
| L-ldh_erm_region | TGTAGAAAAGAGGAAGGAAATAATAAATGGCGGATCCCATGAACAAAAAT |
| | ************************************************** |
| lldh_erm_CAP3_seq_compiled | ATAAAATATTCTCAAAACTTTTTAACGAGTGAAAAAGTACTCAACCAAAT |
| L-ldh_erm_region | ATAAAATATTCTCAAAACTTTTTAACGAGTGAAAAAGTACTCAACCAAAT |
| | ************************************************** |
| lldh_erm_CAP3_seq_compiled | AATAAACAATTGAATTTAAAAGAAACCGATACCGTTTACGAAATTGGAA |
| L-ldh_erm_region | AATAAACAATTGAATTTAAAAGAAACCGATACCGTTTACGAAATTGGAA |
| | ************************************************** |
| lldh_erm_CAP3_seq_compiled | CAGGTAAAGGGCATTTAACGACGAAACTGGCTAAAATAAGTAAACAGGTA |
| L-ldh_erm_region | CAGGTAAAGGGCATTTAACGACGAAACTGGCTAAAATAAGTAAACAGGTA |
| | ************************************************** |
| lldh_erm_CAP3_seq_compiled | ACGTCTATTGAATTAGACAGTCATCTATTCAACTTATCGTCAGAAAAATT |
| L-ldh_erm_region | ACGTCTATTGAATTAGACAGTCATCTATTCAACTTATCGTCAGAAAAATT |
| | ************************************************** |

*Fig. 3C*

```
lldh_erm_CAP3_seq_compiled    AAAACTGAATACTCGTGTCACTTTAATTCACCAAGATATTCTACAGTTTC
L-ldh_erm_region              AAAACTGAATACTCGTGTCACTTTAATTCACCAAGATATTCTACAGTTTC
                              ************************************************** lldh_erm_CAP3_seq_compiled    AATTCCCTAACAAACAGAGGTATAAAATTGTTGGGAGTATTCCTTACCAT
L-ldh_erm_region              AATTCCCTAACAAACAGAGGTATAAAATTGTTGGGAGTATTCCTTACCAT
                              ************************************************** lldh_erm_CAP3_seq_compiled    TTAAGCACACAAATTATTAAAAAAGTGGTTTTTGAAAGCCATGCGTCTGA
L-ldh_erm_region              TTAAGCACACAAATTATTAAAAAAGTGGTTTTTGAAAGCCATGCGTCTGA
                              ************************************************** lldh_erm_CAP3_seq_compiled    CATCTATCTGATTGTTGAAGAAGGATTCTACAAGCGTACCTTGGATATTC
L-ldh_erm_region              CATCTATCTGATTGTTGAAGAAGGATTCTACAAGCGTACCTTGGATATTC
                              ************************************************** lldh_erm_CAP3_seq_compiled    ACCGAACACTAGGGTTGCTCTTGCACACTCAAGTCTCGATTCAGCAATTG
L-ldh_erm_region              ACCGAACACTAGGGTTGCTCTTGCACACTCAAGTCTCGATTCAGCAATTG
                              ************************************************** lldh_erm_CAP3_seq_compiled    CTTAAGCTGCCAGCGGAATGCTTTCATCCTAAACCAAAAGTAAACAGTGT
L-ldh_erm_region              CTTAAGCTGCCAGCGGAATGCTTTCATCCTAAACCAAAAGTAAACAGTGT
                              ************************************************** lldh_erm_CAP3_seq_compiled    CTTAATAAAACTTACCCGCCATACCACAGATGTTCCAGATAAATATTGGA
L-ldh_erm_region              CTTAATAAAACTTACCCGCCATACCACAGATGTTCCAGATAAATATTGGA
                              ************************************************** lldh_erm_CAP3_seq_compiled    AGCTATATACGTACTTTGTTTCAAAATGGGTCAATCGAGAATATCGTCAA
L-ldh_erm_region              AGCTATATACGTACTTTGTTTCAAAATGGGTCAATCGAGAATATCGTCAA
                              ************************************************** lldh_erm_CAP3_seq_compiled    CTGTTTACTAAAAATCAGTTTCATCAAGCAATGAAACACGCCAAAGTAAA
L-ldh_erm_region              CTGTTTACTAAAAATCAGTTTCATCAAGCAATGAAACACGCCAAAGTAAA
                              ************************************************** lldh_erm_CAP3_seq_compiled    CAATTTAAGTACCGTTACTTATGAGCAAGTATTGTCTATTTTTAATAGTT
L-ldh_erm_region              CAATTTAAGTACCGTTACTTATGAGCAAGTATTGTCTATTTTTAATAGTT
                              ************************************************** lldh_erm_CAP3_seq_compiled    ATCTATTATTTAACGGGAGGAAATAATTCTATGAGTCGCTTTTGTAAATT
L-ldh_erm_region              ATCTATTATTTAACGGGAGGAAATAATTCTATGAGTCGCTTTTGTAAATT
                              ************************************************** lldh_erm_CAP3_seq_compiled    TGGAAAGTTACACGTTACTAAAGGGAATTCTCTAGACAGAGTTTGCAGCA
L-ldh_erm_region              TGGAAAGTTACACGTTACTAAAGGGAATTCTCTAGACAGAGTTTGCAGCA
                              ************************************************** lldh_erm_CAP3_seq_compiled    TGGAGCATAACAAACATATCGGGTATATCATTTAATGAGTACTGCAGCAT
L-ldh_erm_region              TGGAGCATAACAAACATATCGGGTATATCATTTAATGAGTACTGCAGCAT
                              ************************************************** lldh_erm_CAP3_seq_compiled    ATGCGGACGCGTCTGCAACACAAATTTCAGAAAGGAAGTAGAAGAAGAAG
L-ldh_erm_region              ATGCGGACGCGTCTGCAACACAAATTTCAGAAAGGAAGTAGAAGAAGAAG
                              **************************************************
```

*Fig. 3D*

```
lldh_erm_CAP3_seq_compiled    TCGTAAATGCTGCTTACAAGATAATAGACAAAAAAGGTGCTACATACTAT
L-ldh_erm_region              TCGTAAATGCTGCTTACAAGATAATAGACAAAAAAGGTGCTACATACTAT
                              ************************************************** lldh_erm_CAP3_seq_compiled    GCTGTGGCAGTTGCAGTAAGAAGGATTGTGGAGTGCATCTTAAGAGATGA
L-ldh_erm_region              GCTGTGGCAGTTGCAGTAAGAAGGATTGTGGAGTGCATCTTAAGAGATGA
                              ************************************************** lldh_erm_CAP3_seq_compiled    AAATTCCATCCTCACAGTATCATCTCCATTAAATGGACAGTACGGCGTGA
L-ldh_erm_region              AAATTCCATCCTCACAGTATCATCTCCATTAAATGGACAGTACGGCGTGA
                              ************************************************** lldh_erm_CAP3_seq_compiled    AAGATGTTTCATTAAGCTTGCCATCTATCGTAGGCAGGAATGGCGTTGCC
L-ldh_erm_region              AAGATGTTTCATTAAGCTTGCCATCTATCGTAGGCAGGAATGGCGTTGCC
                              ************************************************** lldh_erm_CAP3_seq_compiled    AGGATTTTGGACTTGCCTTTATCTGACGAAGAAGTGGAGAAGTTTAGGCA
L-ldh_erm_region              AGGATTTTGGACTTGCCTTTATCTGACGAAGAAGTGGAGAAGTTTAGGCA
                              ************************************************** lldh_erm_CAP3_seq_compiled    TTCAGCAAGTGTCATGGCAGATGTCATAAAACAATTAGATATATAATCAA
L-ldh_erm_region              TTCAGCAAGTGTCATGGCAGATGTCATAAAACAATTAGATATATAATCAA
                              ************************************************** lldh_erm_CAP3_seq_compiled    ATTATGTTGGGAGGCT----------------------------------
L-ldh_erm_region              ATTATGTTGGGAGGCTTCACATATGTGTGGTGGAGGCCTCTTNNNNNNNAT
                              ****************
```

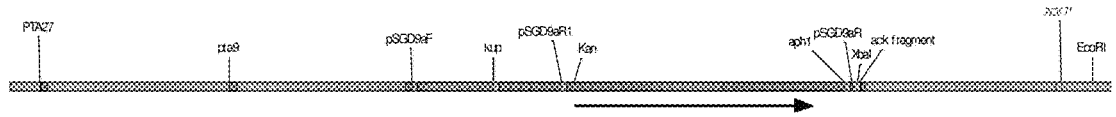

**Sequence alignment – *pta/ack* locus**

```
Line 1: Compiled sequence from ALK1 strain (SEQ ID NO: 10)
Line 2: Expected sequence based on pta/ack sequence and suicide vector pSGD9

Consensus key
* - single, fully conserved residue
  - no consensus

CLUSTAL W (1.81) multiple sequence alignment pta_kan_ack_CAP3_complied     ------------------------------------------------------
pta_kan_ack_region            ATAATAATGCTGCTTCTGTTCTTGACCATTTGTCTATAATAGAAGGAATG pta_kan_ack_CAP3_complied     -AGCGCTGTACGAAATTGCCACTCATTACAGCTACGACAAAGTCTGCTTT
pta_kan_ack_region            CCGCGCTGTACGAAATTGCCACTCATTACAGCTACGACAAAGTCTGCTTT
                               ************************************************* pta_kan_ack_CAP3_complied     TGTCATTTCCATAGACTTTTTTATGTGATATACGTGCCCATTGTGAAGTG
pta_kan_ack_region            TGTCATTTCCATAGACTTTTTTATGTGATATACGTGCCCATTGTGAAGTG
                              ************************************************** pta_kan_ack_CAP3_complied     GATTGTATTCTACAATTAAACCTAATACGCTCATAATATGCGCCTTTCTA
pta_kan_ack_region            GATTGTATTCTACAATTAAACCTAATACGCTCATAATATGCGCCTTTCTA
                              ************************************************** pta_kan_ack_CAP3_complied     AAAAATTATTAATTGTACTTATTATTTTATAAAAAATATGTTAAAATGTA
pta_kan_ack_region            AAAAATTATTAATTGTACTTATTATTTTATAAAAAATATGTTAAAATGTA
                              ************************************************** pta_kan_ack_CAP3_complied     AAATGTGTATACAATATATTTCTTCTTAGTAAGAGGAATGTATAAAAATA
pta_kan_ack_region            AAATGTGTATACAATATATTTCTTCTTAGTAAGAGGAATGTATAAAAATA
                              ************************************************** pta_kan_ack_CAP3_complied     AATATTTTAAAGGAAGGGACGATCTTATGAGCATTATTCAAAACATCATT
pta_kan_ack_region            AATATTTTAAAGGAAGGGACGATCTTATGAGCATTATTCAAAACATCATT
                              ************************************************** pta_kan_ack_CAP3_complied     GAAAAGCTAAAAGCGATAAAAAGAAAATTGTTCTGCCAGAAGGTGCAGA
pta_kan_ack_region            GAAAAGCTAAAAGCGATAAAAAGAAAATTGTTCTGCCAGAAGGTGCAGA
                              **************************************************
```

```
pta_kan_ack_CAP3_complied    ACCCAGGACATTAAAAGCTGCTGAAATAGTTTTAAAAGAAGGGATTGCAG
pta_kan_ack_region           ACCCAGGACATTAAAAGCTGCTGAAATAGTTTTAAAAGAAGGGATTGCAG
                             ************************************************** pta_kan_ack_CAP3_complied    ATTTAGTGCTTCTTGGAAATGAAGATGAGATAAGAAATGCTGCAAAAGAC
pta_kan_ack_region           ATTTAGTGCTTCTTGGAAATGAAGATGAGATAAGAAATGCTGCAAAAGAC
                             ************************************************** pta_kan_ack_CAP3_complied    TTGGACATATCCAAAGCTGAAATCATTGACCCTGTAAAGTCTGAAATGTT
pta_kan_ack_region           TTGGACATATCCAAAGCTGAAATCATTGACCCTGTAAAGTCTGAAATGTT
                             ************************************************** pta_kan_ack_CAP3_complied    TGATAGGTATGCTAATGATTTCTATGAGTTAAGGAAGAACAAAGGAATCA
pta_kan_ack_region           TGATAGGTATGCTAATGATTTCTATGAGTTAAGGAAGAACAAAGGAATCA
                             ************************************************** pta_kan_ack_CAP3_complied    CGTTGGAAAAAGCCAGAGAAACAATCAAGGATAATATCTATTTTGGATGT
pta_kan_ack_region           CGTTGGAAAAAGCCAGAGAAACAATCAAGGATAATATCTATTTTGGATGT
                             ************************************************** pta_kan_ack_CAP3_complied    ATGATGGTTAAAGAAGGTTATGCTGATGGATTGGTATCTGGCGCTATTCA
pta_kan_ack_region           ATGATGGTTAAAGAAGGTTATGCTGATGGATTGGTATCTGGCGCTATTCA
                             ************************************************** pta_kan_ack_CAP3_complied    TGCTACTGCAGATTATTAAGACCTGCATTTCAGATAATTAAAACGGCTC
pta_kan_ack_region           TGCTACTGCAGATTATTAAGACCTGCATTTCAGATAATTAAAACGGCTC
                             ************************************************** pta_kan_ack_CAP3_complied    CAGGAGCAAAGATAGTATCAAGCTTTTTTATAATGGAAGTGCCTAATTGT
pta_kan_ack_region           CAGGAGCAAAGATAGTATCAAGCTTTTTTATAATGGAAGTGCCTAATTGT
                             ************************************************** pta_kan_ack_CAP3_complied    GAATATGGTGAAAATGGTGTATTCTTGTTTGCTGATTGTGCGGTCAACCC
pta_kan_ack_region           GAATATGGTGAAAATGGTGTATTCTTGTTTGCTGATTGTGCGGTCAACCC
                             ************************************************** pta_kan_ack_CAP3_complied    ATCGCCTAATGCAGAAGAACTTGCTTCTATTGCCGTACAATCTGCTAATA
pta_kan_ack_region           ATCGCCTAATGCAGAAGAACTTGCTTCTATTGCCGTACAATCTGCTAATA
                             ************************************************** pta_kan_ack_CAP3_complied    CTGCAAAGAATTTGTTGGGCTTTGAACCAAAAGTTGCCATGCTATCATTT
pta_kan_ack_region           CTGCAAAGAATTTGTTGGGCTTTGAACCAAAAGTTGCCATGCTATCATTT
                             ************************************************** pta_kan_ack_CAP3_complied    TCTACAAAAGGTAGTGCATCACATGAATTAGTAGATAAAGTAAGAAAAGC
pta_kan_ack_region           TCTACAAAAGGTAGTGCATCACATGAATTAGTAGATAAAGTAAGAAAAGC
                             ************************************************** pta_kan_ack_CAP3_complied    GACAGAGATAGCAAAAGAATTGATGCCAGATGTTGCTATCGACGGTGAAT
pta_kan_ack_region           GACAGAGATAGCAGAAGAATTGATGCCAGATGTTGCTATTGACGGTGAAT
                             *********** ******************* ********* pta_kan_ack_CAP3_complied    TGCAATTGGATGCTGCTCTTGTTAAAGAAGTTGCAGAGCTAAAAGCGCCG
pta_kan_ack_region           TGCAATTGGATGCTGCTCTTGTTAAAGAAGTTGCAGAGCTAAAAGCGCCG
                             **************************************************
```

*Fig. 4B*

```
pta_kan_ack_CAP3_complied    GGAAGCAAAGTTGCGGGATGTGCAAATGTGCTTATATTCCCTGATTTACA
pta_kan_ack_region           GGAAGCAAAGTTGCGGGATGTGCAAATGTGCTTATATTCCCTGATTTACA
                             ************************************************** pta_kan_ack_CAP3_complied    AGCTGGTAATATAGGATATAAGCTTGTACAGAGGTTAGCTAAGGCAAATG
pta_kan_ack_region           AGCTGGTAATATAGGATATAAGCTTGTACAGAGGTTAGCTAAGGCAAATG
                             ************************************************** pta_kan_ack_CAP3_complied    CAATTGGACCTATAACACAAGGAATGGGTGCAGGTCGATAAACCCAGCGA
pta_kan_ack_region           CAATTGGACCTATAACACAAGGAATGGGTGCAGGTCGATAAACCCAGCGA
                             ************************************************** pta_kan_ack_CAP3_complied    ACCATTTGAGGTGATAGGTAAGATTATACCGAGGTATGAAAACGAGAATT
pta_kan_ack_region           ACCATTTGAGGTGATAGGTAAGATTATACCGAGGTATGAAAACGAGAATT
                             ************************************************** pta_kan_ack_CAP3_complied    GGACCTTTACAGAATTACTCTATGAAGCGCCATATTTAAAAAGCTACCAA
pta_kan_ack_region           GGACCTTTACAGAATTACTCTATGAAGCGCCATATTTAAAAAGCTACCAA
                             ************************************************** pta_kan_ack_CAP3_complied    GACGAAGAGGATGAAGAGGATGAGGAGGCAGATTGCCTTGAATATATTGA
pta_kan_ack_region           GACGAAGAGGATGAAGAGGATGAGGAGGCAGATTGCCTTGAATATATTGA
                             ************************************************** pta_kan_ack_CAP3_complied    CAATACTGATAAGATAATATATCTTTTATATAGAAGATATCGCCGTATGT
pta_kan_ack_region           CAATACTGATAAGATAATATATCTTTTATATAGAAGATATCGCCGTATGT
                             ************************************************** pta_kan_ack_CAP3_complied    AAGGATTTCAGGGGGCAAGGCATAGGCAGCGCGCTTATCAATATATCTAT
pta_kan_ack_region           AAGGATTTCAGGGGGCAAGGCATAGGCAGCGCGCTTATCAATATATCTAT
                             ************************************************** pta_kan_ack_CAP3_complied    AGAATGGGCAAAGCATAAAAACTTGCATGGACTAATGCTTGAAACCCAGG
pta_kan_ack_region           AGAATGGGCAAAGCATAAAAACTTGCATGGACTAATGCTTGAAACCCAGG
                             ************************************************** pta_kan_ack_CAP3_complied    ACAATAACCTTATAGCTTGTAAATTCTATCATAATTGTGGTTTCAAAATC
pta_kan_ack_region           ACAATAACCTTATAGCTTGTAAATTCTATCATAATTGTGGTTTCAAAATC
                             ************************************************** pta_kan_ack_CAP3_complied    GGCTCCGTCGATACTATGTTATACGCCAACTTTGAAAACAACTTTGAAAA
pta_kan_ack_region           GGCTCCGTCGATACTATGTTATACGCCAACTTTCAAAACAACTTTGAAAA
                             ******************************* ************** pta_kan_ack_CAP3_complied    AGCTGTTTTCTGGTATTTAAGGTTTTAGAATGCAAGGAACAGTGAATTGG
pta_kan_ack_region           AGCTGTTTTCTGGTATTTAAGGTTTTAGAATGCAAGGAACAGTGAATTGG
                             ************************************************** pta_kan_ack_CAP3_complied    AGTTCGTCTTGTTATAATTAGCTTCTTGGGGTATCTTTAAATACTGTAGA
pta_kan_ack_region           AGTTCGTCTTGTTATAATTAGCTTCTTGGGGTATCTTTAAATACTGTAGA
                             ************************************************** pta_kan_ack_CAP3_complied    AAAGAGGAAGGAAATAATAAATGGCTAAAATGAGAATATCACCGGAATTG
pta_kan_ack_region           AAAGAGGAAGGAAATAATAAATGGCTAAAATGAGAATATCACCGGAATTG
                             **************************************************
```

*Fig. 4C*

```
pta_kan_ack_CAP3_complied    AAAAAACTGATCGAAAAATACCGCTGCGTAAAAGATACGGAAGGAATGTC
pta_kan_ack_region           AAAAAACTGATCGAAAAATACCGCTGCGTAAAAGATACGGAAGGAATGTC
                             ************************************************** pta_kan_ack_CAP3_complied    TCCTGCTAAGGTATATAAGCTGGTGGGAGAAAATGAAAACCTATATTTAA
pta_kan_ack_region           TCCTGCTAAGGTATATAAGCTGGTGGGAGAAAATGAAAACCTATATTTAA
                             ************************************************** pta_kan_ack_CAP3_complied    AAATGACGGACAGCCGGTATAAAGGGACCACCTATGATGTGGAACGGGAA
pta_kan_ack_region           AAATGACGGACAGCCGGTATAAAGGGACCACCTATGATGTGGAACGGGAA
                             ************************************************** pta_kan_ack_CAP3_complied    AAGGACATGATGCTATGGCTGGAAGGAAAGCTGCCTGTTCCAAAGGTCCT
pta_kan_ack_region           AAGGACATGATGCTATGGCTGGAAGGAAAGCTGCCTGTTCCAAAGGTCCT
                             ************************************************** pta_kan_ack_CAP3_complied    GCACTTTGAACGGCATGATGGCTGGAGCAATCTGCTCATGAGTGAGGCCG
pta_kan_ack_region           GCACTTTGAACGGCATGATGGCTGGAGCAATCTGCTCATGAGTGAGGCCG
                             ************************************************** pta_kan_ack_CAP3_complied    ATGGCGTCCTTTGCTCGGAAGAGTATGAAGATGAACAAAGCCCTGAAAAG
pta_kan_ack_region           ATGGCGTCCTTTGCTCGGAAGAGTATGAAGATGAACAAAGCCCTGAAAAG
                             ************************************************** pta_kan_ack_CAP3_complied    ATTATCGAGCTGTATGCGGAGTGCATCAGGCTCTTTCACTCCATCGACAT
pta_kan_ack_region           ATTATCGAGCTGTATGCGGAGTGCATCAGGCTCTTTCACTCCATCGACAT
                             ************************************************** pta_kan_ack_CAP3_complied    ATCGGATTGTCCCTATACGAATAGCTTAGACAGCCGCTTAGCCGAATTGG
pta_kan_ack_region           ATCGGATTGTCCCTATACGAATAGCTTAGACAGCCGCTTAGCCGAATTGG
                             ************************************************** pta_kan_ack_CAP3_complied    ATTACTTACTGAATAACGATCTGGACGATGTGGATTGCGAAAACTGGGAA
pta_kan_ack_region           ATTACTTACTGAATAACGATCTGGCCGATGTGGATTGCGAAAACTGGGAA
                             ********************** *********************** pta_kan_ack_CAP3_complied    GAAGACACTCCATTTAAAGATCCGCGCGAGCTGTATGATTTTTTAAAGAC
pta_kan_ack_region           GAAGACACTCCATTTAAAGATCCGCGCGAGCTGTATGATTTTTTAAAGAC
                             ************************************************** pta_kan_ack_CAP3_complied    GGAAAAGCCCGAAGAGGAACTTGTCTTTTCCCACGGCGACCTGGGAGACA
pta_kan_ack_region           GGAAAAGCCCGAAGAGGAACTTGTCTTTTCCCACGGCGACCTGGGAGACA
                             ************************************************** pta_kan_ack_CAP3_complied    GCAACATCTTTGTGAAAGATGGCAAAGTAAGTGGCTTTATTGATCTTGGG
pta_kan_ack_region           GCAACATCTTTGTGAAAGATGGCAAAGTAAGTGGCTTTATTGATCTTGGG
                             ************************************************** pta_kan_ack_CAP3_complied    AGAAGCGGCAGGGCGGACAAGTGGTATGACATTGCCTTCTGCGTCCGGTC
pta_kan_ack_region           AGAAGCGGCAGGGCGGACAAGTGGTATGACATTGCCTTCTGCGTCCGGTC
                             ************************************************** pta_kan_ack_CAP3_complied    GATCAGGGAGGATATCGGGGAAGAACAGTATGTCGAGCTATTTTTTGACT
pta_kan_ack_region           GATCAGGGAGGATATCGGGGAAGAACAGTATGTCGAGCTATTTTTTGACT
                             **************************************************
```

*Fig. 4D*

```
pta_kan_ack_CAP3_complied   TACTGGGGATCAAGCCTGATTGGGAGAAAATAAAAAAATATATTTTACTG
pta_kan_ack_region          TACTGGGGATCAAGCCTGATTGGGAGAAAATAAAATATTATATTTTACTG
                            ****************************** * * ******** pta_kan_ack_CAP3_complied   GATGAATTGTTTTAGTACCTAGATTTAGATGTCTAAAAAGCTTTAACTAC
pta_kan_ack_region          GATGAATTGTTTTAGTACCTAGATTTAGATGTCTAAAAAGCT--------
                            ****************************************** pta_kan_ack_CAP3_complied   AAGCTTTTTAGACATCTAATCTTTTCTGAAGTACATCCGCAACTGTCCAT
pta_kan_ack_region          ------TTTTAGACATCTAATCTTTTCTGAAGTACATCCGCAACTGTCCAT
                                  ****************************************** pta_kan_ack_CAP3_complied   ACTCTGATGTTTTATATCTTTTCTAAAAGTTCGNCTAGATAGGGGTCCCG
pta_kan_ack_region          ACTCTGATGTTTTATATCTTTTCTAAAAGTTCGC-TAGATAGGGGTCCCG
                            ****************************** ************* pta_kan_ack_CAP3_complied   AGCGCCTACGAGGAATTTGTATCGACTCTAGAGCATAGAATATAGCTCCA
pta_kan_ack_region          AGCGCCTACGAGGAATTTGTATCGACTCTAGAGCATAGAAT-TAGCTCCA
                            *************************************** ***** pta_kan_ack_CAP3_complied   CTGCACAATCCTGCTAATATAGAAGGAATTAAAGCTTGCCAGCAAATCAT
pta_kan_ack_region          CTGCACAATCCTGCTAATATAGAAGGAATTAAAGCTTGCCAGCAAATCAT
                            ************************************************** pta_kan_ack_CAP3_complied   GCCAAACGTTCCAATGGTGGCGGTATTTGATACAGCCTTTCATCAGACAA
pta_kan_ack_region          GCCAAACGTTCCAATGGTGGCGGTATTTGATACAGCCTTTCATCAGACAA
                            ************************************************** pta_kan_ack_CAP3_complied   TGCCTGATTATGCATATCTTTATCCAATACCTTATGAATACTACACAAAG
pta_kan_ack_region          TGCCTGATTATGCATATCTTTATCCAATACCTTATGAATACTACACAAAG
                            ************************************************** pta_kan_ack_CAP3_complied   TACAGGATTAGAAGATATGGATTTCATGGCACATCGCATAAATATGTTTC
pta_kan_ack_region          TACAGGATTAGAAGATATGGATTTCATGGCACATCGCATAAATATGTTTC
                            ************************************************** pta_kan_ack_CAP3_complied   AAATAGGGCTGCAGAGATTTTGAATAAACCTATTGAAGATTTGAAAATCA
pta_kan_ack_region          AAATAGGGCTGCAGAGATTTTGAATAAACCTATTGAAGATTTGAAAATCA
                            ************************************************** pta_kan_ack_CAP3_complied   TAACTTGTCATCTTGGAAATGGCTCCAGCATTGCTGCTGTCAAATATGGT
pta_kan_ack_region          TAACTTGTCATCTTGGAAATGGCTCCAGCATTGCTGCTGTCAAATATGGT
                            ************************************************** pta_kan_ack_CAP3_complied   AAATCAATTGACACAAGCATGGGATTTACACCATTAGAAGGTTTGGCTAT
pta_kan_ack_region          AAATCAATTGACACAAGCATGGGATTTACACCATTAGAAGGTTTGGCTAT
                            ************************************************** pta_kan_ack_CAP3_complied   GGGTACACGATCTGGAAGCATAGACCCATCCATCATTTCGTATCTTATGG
pta_kan_ack_region          GGGTACACGATCTGGAAGCATAGACCCATCCATCATTTCGTATCTTATGG
                            ************************************************** pta_kan_ack_CAP3_complied   AAAAGAAAATATAAGCGCTGAAGAAGTAGTAAATATATTAAATAAAAAA
pta_kan_ack_region          AAAAGAAAATATAAGCGCTGAAGAAGTAGTAAATATATTAAATAAAAAA
                            *************************************************
```

*Fig. 4E*

```
pta_kan_ack_CAP3_complied    TCTGGTGTTTACGGTATTTCAGGAATAAGCAGCGATTTTAGAGACTTAGA
pta_kan_ack_region           TCTGGTGTTTACGGTATTTCAGGAATAAGCAGCGATTTTAGAGACTTAGA
                             ************************************************** pta_kan_ack_CAP3_complied    AGATGCCGCCTTTAAAAATGGAGATGAAAGAGCTCAGTTGGCTTTAAATG
pta_kan_ack_region           AGATGCCGCCTTTAAAAATGGAGATGAAAGAGCTCAGTTGGCTTTAAATG
                             ************************************************** pta_kan_ack_CAP3_complied    TGTTTGCATATCGA-GTAAAGAAGACGATTGGCGCTTATGCAGCAGACTA
pta_kan_ack_region           TGTTTGCATATCGAAGTAAAGAAGACGATTGGCGCTTATGCAGCAG-CTA
                             ************ ************************* ** pta_kan_ack_CAP3_complied    TGGGAGGCGTCGATGTCATTGTATTTACAGCAGGTGTGGGTTGGAAAATG
pta_kan_ack_region           TGGGAGGCGTCGATGTCATTGTATTTACAGCAGGTGTTGGT--GAAAATG
                             *********************************** * ******* pta_kan_ack_CAP3_complied    GGTCCA
pta_kan_ack_region           GTCC---
```

*Fig. 4F*

SEQUENCE LISTING

<160> NUMBER OF SEQ ID NOS: 10

<210> SEQ ID NO 1
<211> LENGTH: 34
<212> TYPE: DNA
<213> ORGANISM: Artificial Sequence
<220> FEATURE:
<223> OTHER INFORMATION: pta primer

<400> SEQUENCE: 1
acatgcatgc ccatttgtct ataatagaag gaag        34

<210> SEQ ID NO 2
<211> LENGTH: 24
<212> TYPE: DNA
<213> ORGANISM: Artificial Sequence
<220> FEATURE:
<223> OTHER INFORMATION: pta primer

<400> SEQUENCE: 2
cgtcaacaat atctctatag ctgc        24

<210> SEQ ID NO 3
<211> LENGTH: 29
<212> TYPE: DNA
<213> ORGANISM: Artificial Sequence
<220> FEATURE:
<223> OTHER INFORMATION: ack primer

<400> SEQUENCE: 3
gctctagagc atagaattag ctccactgc        29

<210> SEQ ID NO 4
<211> LENGTH: 34
<212> TYPE: DNA
<213> ORGANISM: Artificial Sequence
<220> FEATURE:
<223> OTHER INFORMATION: ack primer

<400> SEQUENCE: 4
acatgcatgc cgacgcctcc catagctgct gcat        34

<210> SEQ ID NO 5
<211> LENGTH: 34
<212> TYPE: DNA
<213> ORGANISM: Artificial Sequence
<220> FEATURE:
<223> OTHER INFORMATION: aph primer

<400> SEQUENCE: 5
tggatccgcc atttattatt tccttcctct tttc        34

<210> SEQ ID NO 6
<211> LENGTH: 27
<212> TYPE: DNA
<213> ORGANISM: Artificial Sequence
<220> FEATURE:
<223> OTHER INFORMATION: aph primer

<400> SEQUENCE: 6
ttctagatgg ctgcaggtcg ataaacc        27

<210> SEQ ID NO 7
<211> LENGTH: 34
<212> TYPE: DNA
<213> ORGANISM: Artificial Sequence

```
<220> FEATURE:
<223> OTHER INFORMATION: adenine methylase primer

<400> SEQUENCE: 7
gcggatccca tgaacaaaaa tataaaatat tctc                            34

<210> SEQ ID NO 8
<211> LENGTH: 31
<212> TYPE: DNA
<213> ORGANISM: Artificial Sequence
<220> FEATURE:
<223> OTHER INFORMATION: adenine methylase primer

<400> SEQUENCE: 8
gcgaattccc tttagtaacg tgtaactttc c                               31

<210> SEQ ID NO 9
<211> LENGTH: 2778
<212> TYPE: DNA
<213> ORGANISM: Artificial Sequence
<220> FEATURE:
<223> OTHER INFORMATION: L-ldh locus of Thermoanaerobacterium
      saccharolyticum knockout

<400> SEQUENCE: 9
ggaaacgaat agtaaaggaa tggaggcgaa ttaatgagta atgtcgcaat gcaattaata    60
gaaatttgtc ggaaatatgt aaataataat ttaaacataa atgaatttat cgaagacttt   120
caagtgcttt atgaacaaaa gcaagattta ttgacagatg aagaaatgag cttgtttgat   180
gatatttata tggcttgtga atactatgaa caggatgaaa atataagaaa tgaatatcac   240
ttgtatattg gagaaaatga attaagacaa aaagtgcaaa aacttgtaaa aaagttagca   300
gcataataaa ccgctaaggc atgatagcta aagcggtatt tttatgcaat taaaaggatg   360
aaatgatatc tgataaactg cgaaaaagta ttttagaaaa taactataaa gataatattt   420
caaatcaata aggacaaaat aagattaaaa tttagacaat tcatcaaaa ctatgttata    480 atattattaa aggaaaatac atattattta ggaggcgatg taatgagcaa ggtagcaata   540
ataggatctg gttttgtagg tgcaacatcg gcatttacgc tggcattaag tgggactgtg   600
acagatatcg tgctggtgga tttaaacaag gacaaggcta taggcgatgc actggacata   660
agccatggca taccgctaat acagcctgta aatgtgtatg caggtgacta caaagatgtg   720
aaaggcgcag atgtaatagt tgtgacagca ggtgctgctc aaaagccggg agagacacgg   780
cttgaccttg taaagaaaaa tacagccata tttaagtcca tgatacctga gcttttaaag   840
tacaatgaca aggccatata tttgattgtg acaaatcccg tagatatact gacgtacgtt   900
acatacaaga tttctggact tccatggggc agagttttg gttctggcac cgttcttgac   960
agctcaaggt ttagataccct tttaagcaag gactgctgca ggtcgataaa cccagcgaac  1020
catttgaggt gataggtaag attataccga ggtatgaaaa cgagaattgg acctttacag  1080
aattactcta tgaagcgcca tatttaaaaa gctaccaaga cgaagaggat gaagaggatg  1140
aggaggcaga ttgccttgaa tatattgaca atactgataa gataatatat cttttatata  1200
gaagatatcg ccgtatgtaa ggatttcagg gggcaaggca taggcagcgc gcttatcaat  1260
atatctatag aatgggcaaa gcataaaaac ttgcatggac taatgcttga aacccaggac  1320
aataacctta tagcttgtaa attctatcat aattgtggtt tcaaaatcgg ctccgtcgat  1380
actatgttat acgccaactt tgaaacaac tttgaaaaag ctgttttctg gtatttaagg   1440
ttttagaatg caaggaacag tgaattggag ttcgtcttgt tataattagc ttcttggggt  1500
```

| | |
|---|---|
| atctttaaat actgtagaaa agaggaagga aataataaat ggcggatccc atgaacaaaa | 1560 |
| atataaaata ttctcaaaac tttttaacga gtgaaaagt actcaaccaa ataataaaac | 1620 |
| aattgaattt aaaagaaacc gataccgttt acgaaattgg aacaggtaaa gggcatttaa | 1680 |
| cgacgaaact ggctaaaata agtaaacagg taacgtctat tgaattagac agtcatctat | 1740 |
| tcaacttatc gtcagaaaaa ttaaaactga atactcgtgt cactttaatt caccaagata | 1800 |
| ttctacagtt tcaattccct aacaaacaga ggtataaaat tgttgggagt attccttacc | 1860 |
| atttaagcac acaaattatt aaaaagtgg tttttgaaag ccatgcgtct gacatctatc | 1920 |
| tgattgttga agaaggattc tacaagcgta ccttggatat tcaccgaaca ctagggttgc | 1980 |
| tcttgcacac tcaagtctcg attcagcaat tgcttaagct gccagcggaa tgctttcatc | 2040 |
| ctaaaccaaa agtaaacagt gtcttaataa aacttacccg ccataccaca gatgttccag | 2100 |
| ataaatattg gaagctatat acgtactttg tttcaaaatg ggtcaatcga gaatatcgtc | 2160 |
| aactgtttac taaaaatcag tttcatcaag caatgaaaca cgccaaagta aacaatttaa | 2220 |
| gtaccgttac ttatgagcaa gtattgtcta tttttaatag ttatctatta tttaacggga | 2280 |
| ggaaataatt ctatgagtcg cttttgtaaa tttggaaagt tacacgttac taaagggaat | 2340 |
| tctctagaca gagtttgcag catggagcat aacaaacata tcgggtatat catttaatga | 2400 |
| gtactgcagc atatgcggac gcgtctgcaa cacaaatttc agaaaggaag tagaagaaga | 2460 |
| agtcgtaaat gctgcttaca agataataga caaaaaaggt gctacatact atgctgtggc | 2520 |
| agttgcagta agaaggattg tggagtgcat cttaagagat gaaaattcca tcctcacagt | 2580 |
| atcatctcca ttaaatggac agtacggcgt gaaagatgtt tcattaagct tgccatctat | 2640 |
| cgtaggcagg aatggcgttg ccaggatttt ggacttgcct ttatctgacg aagaagtgga | 2700 |
| gaagtttagg cattcagcaa gtgtcatggc agatgtcata aaacaattag atatataatc | 2760 |
| aaattatgtt gggaggct | 2778 |

<210> SEQ ID NO 10
<211> LENGTH: 3355
<212> TYPE: DNA
<213> ORGANISM: Artificial Sequence
<220> FEATURE:
<223> OTHER INFORMATION: pta/ack locus of Thermoanaerobacterium
    saccharolyticum knockout
<220> FEATURE:
<221> NAME/KEY: misc_feature
<222> LOCATION: (2632)..(2634)
<223> OTHER INFORMATION: n is a, c, g or t
<220> FEATURE:
<221> NAME/KEY: misc_feature
<222> LOCATION: (3262)..(3265)
<223> OTHER INFORMATION: n is a, c, g, or t

<400> SEQUENCE: 10

| | |
|---|---|
| agcgctgtac gaaattgcca ctcattacag ctacgacaaa gtctgctttt gtcatttcca | 60 |
| tagactttt tatgtgatat acgtgcccat tgtgaagtgg attgtattct acaattaaac | 120 |
| ctaatacgct cataatatgc gcctttctaa aaaattatta attgtactta ttatttata | 180 |
| aaaaatatgt taaatgtaa aatgtgtata caatatattt cttcttagta agaggaatgt | 240 |
| ataaaaataa atattttaaa ggaagggacg atcttatgag cattattcaa acatcattg | 300 |
| aaaaagctaa aagcgataaa aagaaaattg ttctgccaga aggtgcagaa cccaggacat | 360 |
| taaaagctgc tgaaatagtt ttaaagaag ggattgcaga tttagtgctt cttggaaatg | 420 |
| aagatgagat aagaaatgct gcaaaagact tggacatatc caaagctgaa atcattgacc | 480 |

```
ctgtaaagtc tgaaatgttt gataggtatg ctaatgattt ctatgagtta aggaagaaca    540
aaggaatcac gttggaaaaa gccagagaaa caatcaagga taatatctat tttggatgta    600
tgatggttaa agaaggttat gctgatggat tggtatctgg cgctattcat gctactgcag    660
atttattaag acctgcattt cagataatta aaacggctcc aggagcaaag atagtatcaa    720
gcttttttat aatggaagtg cctaattgtg aatatggtga aaatggtgta ttcttgtttg    780
ctgattgtgc ggtcaaccca tcgcctaatg cagaagaact tgcttctatt gccgtacaat    840
ctgctaatac tgcaaagaat tgttgggct ttgaaccaaa agttgccatg ctatcatttt    900
ctacaaaagg tagtgcatca catgaattag tagataaagt aagaaaagcg acagagatag    960
caaaagaatt gatgccagat gttgctatcg acggtgaatt gcaattggat gctgctcttg    1020
ttaaagaagt tgcagagcta aaagcgccgg gaagcaaagt tgcgggatgt gcaaatgtgc    1080
ttatattccc tgatttacaa gctggtaata taggatataa gcttgtacag aggttagcta    1140
aggcaaatgc aattggacct ataacacaag gaatgggtgc aggtcgataa acccagcgaa    1200
ccatttgagg tgataggtaa gattataccg aggtatgaaa acgagaattg gacctttaca    1260
gaattactct atgaagcgcc atatttaaaa agctaccaag acgaagagga tgaagaggat    1320
gaggaggcag attgccttga atatattgac aatactgata agataatata tcttttatat    1380
agaagatatc gccgtatgta aggatttcag ggggcaaggc ataggcagcg cgcttatcaa    1440
tatatctata gaatgggcaa agcataaaaa cttgcatgga ctaatgcttg aaacccagga    1500
caataacctt atagcttgta aattctatca taattgtggt ttcaaaatcg gctccgtcga    1560
tactatgtta tacgccaact ttgaaaacaa ctttgaaaaa gctgttttct ggtatttaag    1620
gttttagaat gcaaggaaca gtgaattgga gttcgtcttg ttataattag cttcttgggg    1680
tatctttaaa tactgtagaa aagaggaagg aaataataaa tggctaaaat gagaaatatca    1740 ccggaattga aaaaactgat cgaaaaatac cgctgcgtaa aagatacgga aggaatgtct    1800
cctgctaagg tatataagct ggtgggagaa aatgaaaacc tatatttaaa aatgacggac    1860
agccggtata aagggaccac ctatgatgtg aacgggaaa aggacatgat gctatggctg    1920
gaaggaaagc tgcctgttcc aaaggtcctg cactttgaac ggcatgatgg ctggagcaat    1980
ctgctcatga gtgaggccga tggcgtcctt tgctcggaag agtatgaaga tgaacaaagc    2040
cctgaaaaga ttatcgagct gtatgcgag tgcatcaggc tctttcactc catcgacata    2100
tcggattgtc cctatacgaa tagcttagac agccgcttag ccgaattgga ttacttactg    2160
aataacgatc tggacgatgt ggattgcgaa aactgggaag aagacactcc atttaaagat    2220
ccgcgcgagc tgtatgattt tttaaagacg gaaaagcccg aagaggaact tgtcttttcc    2280
cacggcgacc tgggagacag caacatcttt gtgaaagatg gcaaagtaag tggctttatt    2340
gatcttggga agcggcag gcggacaag tggtatgaca ttgccttctg cgtccggtcg    2400
atcagggagg atatcgggga agaacagtat gtcgagctat tttttgactt actggggatc    2460
aagcctgatt gggagaaaat aaaaaaatat attttactgg atgaattgtt ttagtaccta    2520
gatttagatg tctaaaaagc tttaactaca agcttttag acatctaatc ttttctgaag    2580
tacatccgca actgtccata ctctgatgtt ttatatcttt tctaaaagtt cgnctagata    2640
ggggtcccga gcgcctacga ggaatttgta tcgactctag agcatagaat atagctccac    2700
tgcacaatcc tgctaatata gaaggaatta aagcttgcca gcaaatcatg ccaaacgttc    2760
caatggtggc ggtatttgat acagcctttc atcagacaat gcctgattat gcatatcttt    2820
```

```
atccaataac  ttatgaatac  tacacaaagt  acaggattag  aagatatgga  tttcatggca    2880
catcgcataa  atatgtttca  aatagggctg  cagagatttt  gaataaacct  attgaagatt    2940
tgaaaatcat  aacttgtcat  cttggaaatg  gctccagcat  tgctgctgtc  aaatatggta    3000
aatcaattga  cacaagcatg  ggatttacac  cattagaagg  tttggctatg  ggtacacgat    3060
ctggaagcat  agaccatcc   atcatttcgt  atcttatgga  aaaagaaaat  ataagcgctg    3120
aagaagtagt  aaatatatta  aataaaaaat  ctggtgttta  cggtatttca  ggaataagca    3180
gcgattttag  agacttagaa  gatgccgcct  ttaaaaatgg  agatgaaaga  gctcagttgg    3240
ctttaaatgt  gtttgcatat  cgangtaaag  aagacgattg  gcgcttatgc  agcagactat    3300
gggaggcgtc  gatgtcattg  tatttacagc  aggtgtgggt  tggaaaatgg  gtcca         3355
```

THERMOPHILIC ORGANISMS FOR CONVERSION OF LIGNOCELLULOSIC BIOMASS TO ETHANOL

GOVERNMENT INTERESTS

The United States Government may have certain rights in the present invention as research relevant to its development was funded by National Institute of Standards and Technology (NIST) contract number 60NANB1D0064.

RELATED APPLICATIONS

This application is a U.S. National phase application of PCT/US2007/067941, filed May 1, 2007, which claims priority to PCT/US2006/042442, filed Oct. 31, 2006, which claimed priority to U.S. Patent Application 60/796,380, filed May 1, 2006. Each of these applications mentioned above is incorporated herein by reference. This application is also a continuation-in-part of U.S. patent application Ser. No. 12/090,745, filed Apr. 18, 2008, which is a U.S. National Phase Application of PCT/US2006/042442, filed Oct. 31, 2006, which claims priority to U.S. Patent Application No. 60/731,674, filed Oct. 31, 2005, and to U.S. Patent Application No. 60/796,380, filed May 1, 2006.

BACKGROUND

1. Field of the Invention

The present invention pertains to the field of biomass processing to produce ethanol. In particular, novel thermophilic organisms that consume a variety of biomass derived substrates and produce ethanol in high yield are disclosed, as well as processes for the production and use of the organisms.

2. Description of the Related Art

Biomass represents an inexpensive and readily available cellulolytic substrate from which sugars may be produced. These sugars may be used alone or fermented to produce alcohols and other products. Among bioconversion products, interest in ethanol is high because it may be used as a renewable domestic fuel.

Significant research has been performed in the areas of reactor design, pretreatment protocols and separation technologies, so that bioconversion processes are becoming economically competitive with petroleum fuel technologies. However, it is estimated that the largest cost savings may be obtained when two or more process steps are combined. For example, simultaneous saccharification and fermentation (SSF) and simultaneous saccharification and co-fermentation (SSCF) processes combine an enzymatic saccharification step with fermentation in a single reactor or continuous process apparatus. In an SSF process, end-product inhibition is removed as the soluble sugars are continually fermented into ethanol. When multiple organisms are used to provide a variety of hydrolysis products, the SSF process is usually referred to as a simultaneous saccharification and co-fermentation (SSCF) process. In addition to savings associated with shorter reaction times and reduced capital costs, co-fermentation processes may also provide improved product yields because certain compounds that would otherwise accrue at levels that inhibit metabolysis or hydrolysis are consumed by the co-fermenting organisms. In one such example, β-glucosidase ceases to hydrolyze cellobiose in the presence of glucose and, in turn, the build-up of cellobiose impedes cellulose degradation. An SSCF process involving co-fermentation of cellulose and hemicellulose hydrolysis products may alleviate this problem by converting glucose into one or more products that do not inhibit the hydrolytic activity of β-glucosidase.

Consolidated bioprocessing (CBP) involves four biologically-mediated events: (1) enzyme production, (2) substrate hydrolysis, (3) hexose fermentation and (4) pentose fermentation. These events may be performed in a single step. This strategy requires a microorganism that utilizes cellulose and hemicellulose. Development of CBP organisms could potentially result in very large cost reductions as compared to the more conventional approach of producing saccharolytic enzymes in a dedicated process step. CBP processes that utilize more than one organism to accomplish the four biologically-mediated events are referred to as consolidated bioprocessing co-culture fermentations.

Some bacteria have the ability to convert pentose sugars into hexose sugars, and to ferment the hexose sugars into a mixture of organic acids and other products by glycolysis. The glycolytic pathway begins with conversion of a six-carbon glucose molecule into two three-carbon molecules of pyruvate. Pyruvate may then be converted to lactate by the action of lactate dehydrogenase ("ldh"), or to acetyl coenzyme A ("acetyl-CoA") by the action of pyruvate dehydrogenase or pyruvate-ferredoxin oxidoreductase. Acetyl-CoA is further converted to acetate by phosphotransacetylase and acetate kinase, or reduced to ethanol by acetaldehyde dehydrogenase ("AcDH") and alcohol dehydrogenase ("adh"). Overall, the performance of ethanol-producing organisms is compromised by production of organic products other than ethanol, and particularly by ldh-mediated conversion of pyruvate to lactate, and by conversion of acetyl-CoA to acetate by phosphotransacetylase and acetate kinase.

Metabolic engineering of bacteria has recently resulted in the creation of a knockout of lactate dehydrogenase in the thermophilic, anaerobic, Gram-positive bacterium *T. saccharolyticum*. See, Desai, S. G.; Guerinot, M. L.; Lynd, L. R. "Cloning of L-lactate dehydrogenase and elimination of lactic acid production via gene knockout in *Thermoanaerobacterium saccharolyticum* JW/SL-YS485" Appl. Microbiol. Biotechnol. 65: 600-605, 2004.

Although the knockout of ldh constitutes an advance in the art, it is problematic for some uses of this organism in that this strain of *T. saccharolyticum* continues to make organic acid—in particular, acetic acid.

SUMMARY

The present instumentalities advance the art and overcome the problems outlined above by providing thermophilic, anaerobic bacteria that consume a variety of biomass derived substrates and produce ethanol in near theoretical yields. Methods for producing ethanol using the organisms are also disclosed.

The instrumentalities reported herein result in the knockout of various genes either singly or in combination, where such genes in the native organism would otherwise result in the formation of organic acids. For example, there may be knockouts of: (a) acetate kinase and/or phosphotransacetylase and (b) lactate dehydrogenase (ldh), acetate kinase (ack) and phosphotransacetylase (pta) in *T. saccharolyticum* JW/SL-YS485. Although the results reported herein are for *T. saccharolyticum*, the methods and materials also apply to other members of the *Thermoanaerobacter* genus including *Thermoanaerobacterium thermosulfurigenes*, *Thermoan-*

*aerobacterium aotearoense, Thermoanaerobacterium polysaccharolyticum, Thermoanaerobacterium zeae, Thermoanaerobacterium thermosaccharolyticum,* and *Thermoanaerobacterium xylanolyticum.* The methods and materials are useful generally in the field of metabolically engineered, thermophilic, Gram-positive bacteria.

In one embodiment, an isolated organism, which does not express pyruvate decarboxylase, ferments a cellulolytic substrate to produce ethanol in a concentration that is at least 90% of a theoretical yield.

In one embodiment, a Gram-positive bacterium, that in a native state contains at least one gene which confers upon the Gram-positive bacterium an ability to produce acetic acid as a fermentation product, is transformed to eliminate expression of the at least one gene. The bacterium may be a *Thermoanaerobacter*, such as *Thermoanaerobacterium saccharolyticum*. The gene which confers upon the Gram-positive bacterium an ability to produce acetic acid as a fermentation product may code for expression of acetate kinase and/or phosphotransacetylase.

In another embodiment, the Gram-positive bacterium may be further transformed to eliminate expression of one or more genes that confer upon the Gram-positive bacterium the ability to produce lactic acid as a fermentation product. For example, the gene that confers the ability to produce lactic acid may be lactate dehydrogenase.

In one embodiment, a method for producing ethanol includes transforming a native organism to produce a Gram-positive bacterium that has been transformed to eliminate expression of all genes that confer upon the Gram-positive bacterium the ability to produce organic acids as fermentation products, to produce a transformed bacterial host, and culturing the transformed bacterial host in medium that contains a substrate including a material selected from the group consisting of glucose, xylose, cellobiose, sucrose, xylan, starch, and combinations thereof under suitable conditions for a period of time sufficient to allow saccharification and fermentation of the substrate.

In one embodiment, a biologically pure culture of a microorganism designated ALK1 and deposited with the ATCC under Patent Deposit Designation No. PTA-7206 is described.

In one embodiment an isolated polynucleotide comprises (a) a sequence of SEQ ID NO: 10, or (b) a sequence of SEQ ID NO: 9 and SEQ ID NO: 10, or (c) a sequence having at least about 90% sequence identity with the sequence of (a) or (b). A vector comprising the isolated polynucleotide of (a), (b), or (c) is described, as well as a host cell genetically engineered to express a compliment of the polynucleotide of (a), (b), or (c). In another embodiment, an isolated polynucleotide comprises a sequence having at least about 95% sequence identity with the sequence of (a) or (b). In yet another embodiment, an isolated polynucleotide comprises a sequence having at least about 98%, or at least about 99%, sequence identity with the sequence of (a) or (b).

In one embodiment, a method of producing ethanol includes culturing a mutant bacterium expressing a compliment of the isolated polynucleotide of (a), (b), or (c) in medium containing a substrate selected from the group consisting of glucose, xylose, cellobiose, sucrose, xylan, starch, and combinations thereof under suitable conditions for a period of time sufficient to allow fermentation of the substrate to ethanol.

In one embodiment, a method for producing ethanol includes providing within a reaction vessel, a reaction mixture comprising lignocellulosic substrate, cellulase and a fermentation agent. The fermentation agent comprises a Gram-positive bacterium that has been transformed to eliminate expression of at least one gene that confers upon the Gram-positive bacterium, in a native state, an ability to produce acetic acid as a fermentation product. The reaction mixture is reacted under suitable conditions for a period of time sufficient to allow saccharification and fermentation of the lignocellulosic substrate.

BRIEF DESCRIPTION OF THE DRAWINGS

FIGS. 3A-3E shows a comparison of experimental and expected polynucleotide sequences for the ldh region of the suicide vector pSGD9 (SEQ ID NO: 9) integrated into the genome of *T. saccharolyticum*.

FIGS. 4A-4F shows a comparison of experimental and expected polynucleotide sequences for the pta/ack region of the suicide vector pSGD8-Erm (SEQ ID NO: 10) integrated into the genome of *T. saccharolyticum*.

DETAILED DESCRIPTION

There will now be shown and described methods for engineering and utilizing thermophilic, anaerobic, Gram-positive bacteria in the conversion of biomass to ethanol.

As used herein, an organism is in "a native state" if it is has not been genetically engineered or otherwise manipulated by the hand of man in a manner that intentionally alters the genetic and/or phenotypic constitution of the organism. For example, wild-type organisms may be considered to be in a native state.

Complete elimination of organic acid production from a *T. saccharolyticum* in a native state was achieved using two site-directed DNA homologous recombination events. The mutant strain, *Thermoanaerobacterium saccharolyticum* JW/SL-YS485 ALK1 ("ALK1") produces near theoretical amounts of ethanol at low substrate feedings in batch culture with a temperature in a range of about 30-66° C. and a pH in a range of about 3.85-6.5. In one embodiment, ethanol yield is at least about 90% of the theoretical maximum. ALK1, and its decendents, have the potential to contribute significant savings in the lignocellulosic biomass to ethanol conversion due to its growth conditions, which are substantially optimal for cellulase activity in SSF and SSCF processes. For example, optimal cellulase activity parameters include a pH between 4-5 and temperature between 40-50° C. Additionally, it is unnecessary to adjust the pH of the fermentation broth when knockout organisms, which lack the ability to produce organic acids, are used. ALK1, and similar organisms, may also be suitable for a consolidated bioprocessing co-culture fermentation where the knockout organism would convert pentoses to ethanol, and cellulose would be degraded by a cellulolytic organism such as *C. thermocellum*.

Operating either an SSF, SSCF or CBP process at thermophilic temperatures offers several important benefits over conventional mesophilic fermentation temperatures of 30-37° C. In particular, enzyme concentrations necessary to achieve a given amount of conversion may be reduced due to higher enzyme activity at thermophilic temperatures. As a result, costs for a process step dedicated to cellulase production are substantially reduced (e.g., 2-fold or more) for thermophilic SSF and SSCF, and are eliminated for CBP. Costs associated with fermentor cooling and also heat exchange before and after fermentation are also expected to be reduced for thermophilic SSF, SSCF and CBP. Finally, processes featuring thermophilic biocatalysts may be less susceptible to microbial contamination as compared to processes featuring conventional mesophilic biocatalysts.

Figure 1:
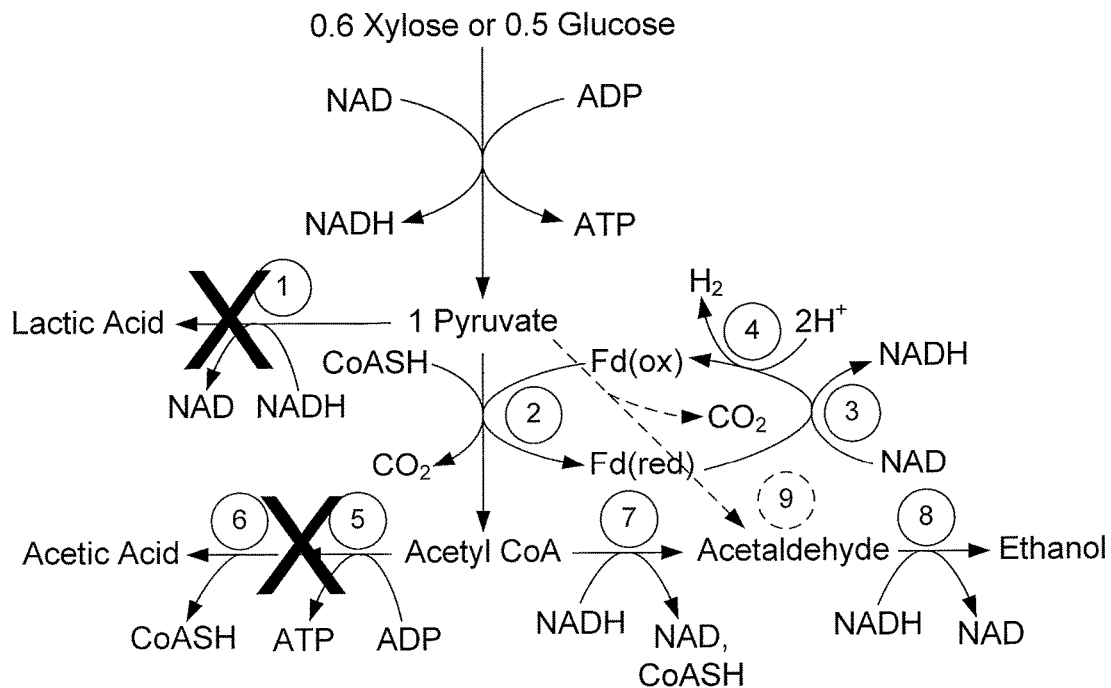
FIG. 1 shows reactions of the glycolytic pathway.
Figure 2:
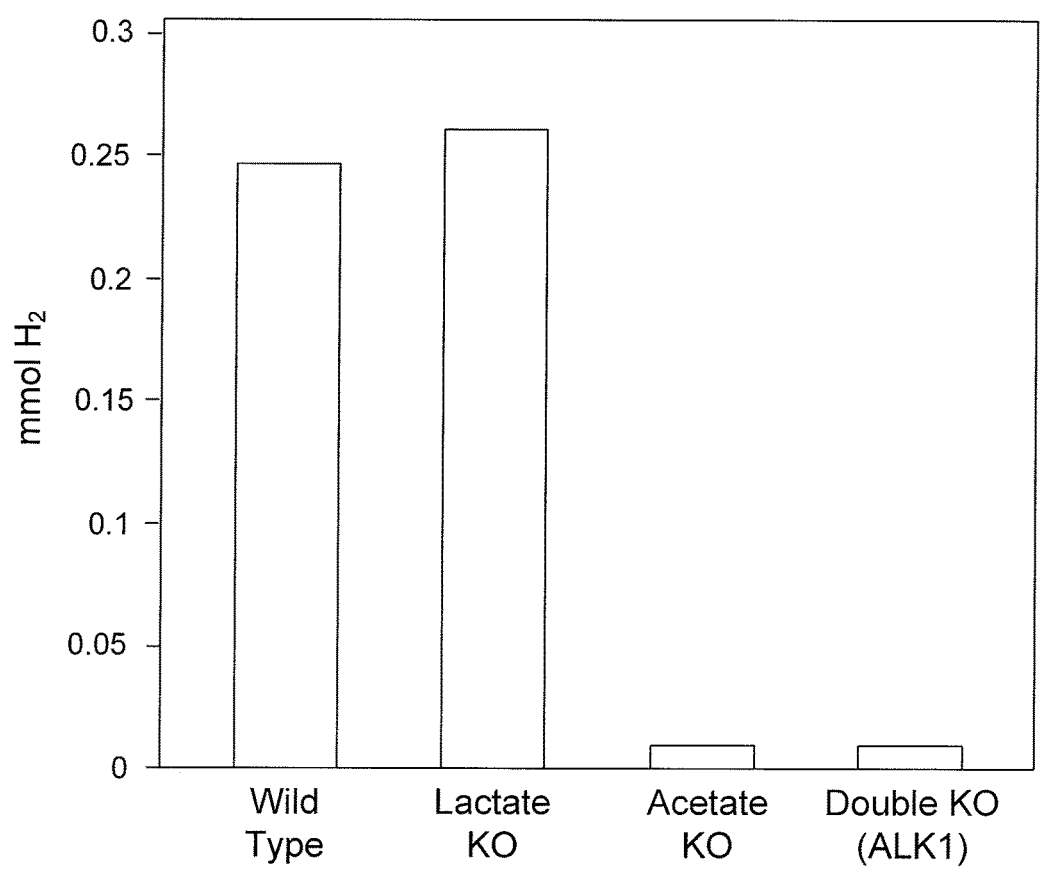
FIG. 2 shows hydrogen production in wild-type *T. saccharolyticum* compared to various knockout strains of *T. saccharolyticum*.

In contrast to known "homoethanol-fermenting" microorganisms, such as naturally-occurring *Saccharomyces cerevisiae* and *Zymomonas mobilis*, and recombinant strains of *Escherichia coli* and *Klebsiella oxytoca*, the presently disclosed organisms do not depend on conversion of pyruvate to acetaldehyde via the action of pyruvate decarboxylase (see FIG. 1, 9). In fact, bacteria belonging to the *Thermoanaerobacter* genus do not express pyruvate decarboxylase in the native state. From the reactions of the glycolytic pathway shown in FIG. 1, it can be observed that pyruvate may be metabolized to acetyl-CoA, carbon dioxide, and reduced ferredoxin by the enzyme pyruvate-ferredoxin oxidoreductase 2. However, in order to produce ethanol as the only fermentation product, the electrons carried by reduced ferredoxin must all be transferred to NAD via NAD:ferredoxin oxidoreductase 3 to form NADH. NADH is subsequently oxidized back to NAD in the course of the two-step reduction of acetyl-CoA to ethanol by acetaldehyde dehydrogenase 7 and alcohol dehydrogenase 8. Evidence of the efficient utilization of NADH may be observed in FIG. 2 as a decrease in production of $H_2$ by both the acetate knockout organism, which is unable to express ack and pta, and the double knockout organism (ALK1), which is unable to express ack, pta and ldh. These organisms provide the first demonstration of stoichiometric electron transfer from reduced ferredoxin to NAD, and subsequently to ethanol.

The above-described pathway, which produces stoichiometric ethanol yields in organisms that do not possess the ability to express PDC, is in contrast to the pathway employed in all previously-described homoethanol-fermenting strains. Previously-described strains utilize endogenous pyruvate decarboxylase (PDC), or are engineered to express exogenous PDC. Since expression of PDC is rare in the microbial world, the ability to redirect electron flow by virtue of modifications to carbon flow has broad implications. For example, this approach could be used to produce high ethanol yields in strains other than *T. saccharolyticum* and/or to produce solvents other than ethanol. In particular, Gram-positive bacteria, such as members of the *Thermoanaerober* genus; *Clostridium thermocellum* and other thermophilic and mesophilic Clostridia; thermophilic and mesophilic *Bacillus* species; Gram-negative bacteria, such as *Escherichia coli* and *Klebsiella oxytoca*; *Fibrobacter succinogenes* and other *Fibrobacter* species; *Thermoga neopolitana* and other *Thermotoga* species; and anaerobic fungi including *Neocallimatix* and *Piromyces* species lack the ability to express PDC, and may benefit from the disclosed instrumentalities.

It will be appreciated that lignocellulosic material that is saccharified to produce one or more of glucose, xylose, mannose, arabinose, galactose, fructose, cellobiose, sucrose, maltose, xylan, mannan and starch may be utilized by the disclosed organisms. In various embodiments, the lignocellulosic biomass comprises wood, corn stover, sawdust, bark, leaves, agricultural and forestry residues, grasses such as switchgrass, ruminant digestion products, municipal wastes, paper mill effluent, newspaper, cardboard, or combinations thereof.

Example 1

Production of the ALK1 Strain

Materials and Methods

*Thermoanaerobacterium saccharolyticum* strain JW/SL-YS485 (DSM 8691) is a thermophilic, anaerobic bacteria isolated from the West Thumb Basin in Yellowstone National Park, Wyo. (Lui, S. Y; Gherardini, F. C.; Matuschek, M.; Bahl, H.; Wiegel, J. "Cloning, sequencing, and expression of the gene encoding a large S-layer-associated endoxylanase from *Thermoanaerobacterium* sp strain JW/SL-YS485 in *Escherichia coli*" J. Bacteriol. 178: 1539-1547, 1996; Mai, V.; Wiegel, J. "Advances in development of a genetic system for *Thermoanaerobacterium* spp: Expression of genes encoding hydrolytic enzymes, development of a second shuttle vector, and integration of genes into the chromosome" Appl. Environ. Microbiol. 66: 4817-4821, 2000). It grows in a temperature range of 30-66° C. and in a pH range of 3.85-6.5. It consumes a variety of biomass derived substrates including the monosaccharides glucose and xylose, the disaccharides cellobiose and sucrose, and the polysaccharides xylan and starch, but not cellulose. The organism produces ethanol as well as the organic acids lactic acid and acetic acid as primary fermentation products.

Cloning and Sequencing

The lactate dehydrogenase (L-ldh), phosphotransacetylase (pta), and acetate kinase (ack) genes were identified and sequenced using standard techniques, as reported previously for L-ldh (Desai, 2004). Degenerate primers were made using the CODE-HOP algorithm (Rose, T.; Schultz, E.; Henikoff, J.; Pietrokovski, S.; McCallum, C.; Henikoff, S. "Consensus-degenerate hybrid oligonucleotide primers for amplification of distantly-related sequences" Nucleic Acids Research, 26(7):1628-1635, 1 Apr. 1998) and PCR reactions were performed to obtain the DNA sequence between conserved regions. The gene fragments outside of the conserved regions were sequenced directly from genomic DNA using ThermoFidelase (Fidelity Systems, Gaithersburg, Md.) enzyme with BigDye Terminator kit v3.1 (ABI, Foster City Calif.).

Construction of Suicide Vectors

Acetate Kinase and Phosphotransacetylase Knockout Vector, pSGD9

Standard cloning techniques were followed (Sambrook). The 6.2 kb suicide vector pSGD9 was based on pBLUESCRIPT II SK (+) (Stratagene) using a design approach similar to that reported earlier (Desai, 2004; Mai, 2000). Gene fragments of the pta/ack sequence, pta-up (~1.2 kb) and ack-down (~0.6 kb), were amplified from genomic DNA using primer pairs SEQ ID NOS: 1-2, and SEQ ID NOS: 3-4. PCR amplification was performed with pfu DNA polymerase and the fragments were extracted from a 1% electrophoresis gel. Fragments pta-up and ack-down were then A-tailed with Taq polymerase and cloned into TOPO pCR2.1 (Invitrogen, Carlsbad, Calif.). A 1.5 kb fragment containing the kanamycin marker was obtained from a PstI/XbaI digest of pIKM1 and subcloned into pBLUE-SCRIPT II SK (+). TOPO containing pta-up was digested with XhoI/BsiHKAI and subcloned into XhoI/PstI digested pBLUESCRIPT II SK (+), upstream of the previously subcloned kanamycin marker. TOPO containing ack-down was digested with XbaI/SphI and subcloned into pUC19 (Invitrogen). XbaI/AflIII fragment containing ack-down was digested and subcloned downstream of the kanamycin marker to obtain the final construct pSGD9.

Lactate Dehydrogenase Knockout Vector with Erythromycin Resistance, pSGD8-Erm

The 5.5 kb suicide vector pSGD8-Erm was based on the plasmid pSGD8 as produced by Desai et al. 2004. In place of the aph kanamycin antibiotic marker, a fusion gene based on the aph promoter from the plasmid pIKM1 and the adenine methylase gene conferring erythromycin resistance from the plasmid pCTC1 (Klapatch, T. R.; Guerinot, M. L.; Lynd, L. R. "Electrotransformation of Clostridium thermosaccharolyticum" J. Ind. Microbiol. 16(6): 342-7, June 1996) were used for selection. PCR gene fragments were created using pfu polymerase (Stategene) and the primers SEQ ID NOS: 5-6 for the aph promoter and SEQ ID NOS: 7-8 for the adenine methylase open reading frame. Fragments were digested with XbaI/BamHI (aph fragment) and BamHIH/EcoRI (adenine methylase) and ligated into the multiple cloning site of pIKM1. This fusion gene was then excised with BseRI/EcoRI and ligated into similarly digested pSGD8.

Transformation of T. Saccharolyticum

Transformation of T. saccharolyticum was performed interchangeably with two methods, the first as previously described (Mai, V.; Lorenz, W.; Weigel, J. "Transformation of Thermoanaerobacterium sp. strain JW/SL-YS485 with plasmid PIKM1 conferring kanamycin resistance" FEMS Microbiol. Lett. 148: 163-167, 1997) and the second with several modifications following cell harvest and based on the method developed for Clostridium thermocellum (Tyurin, M. V.; Desai, S. G.; Lynd, L. R. "Electrotransformation of Clostridium thermocellum" Appl. Environ. Microbiol. 70(2): 883-890, 2004). Cells were grown overnight using pre-reduced medium DSMZ 122 in sterile disposable culture tubes inside an anaerobic chamber in an incubator maintained at 55° C. Thereafter, cells were sub-cultured with 4 µg/ml isonicotonic acid hydrazide (isoniacin), a cell wall weakening agent (Hermans, J.; Boschloo, J. G.; de Bont, J. A. M. "Transformation of M aurum by electroporation: the use of glycine, lysozyme and isonicotinic acid hydrazide in enhancing transformation efficiency" FEMS Microbiol. Lett. 72, 221-224, 1990), added to the medium after the initial lag phase. Exponential phase cells were harvested and washed with pre-reduced cold sterile 200 mM cellobiose solution, and resuspended in the same solution and kept on ice. Extreme care was taken following the harvesting of cells to keep them cold (approximately 4° C.) at all times including the time during centrifugation.

Samples composed of 90 µl of the cell suspension and 2 to 6 µl of pSGD9 or pSGD8-Erm (1 to 3 µg) added just before pulse application, were placed into sterile 2 ml polypropylene microcentrifuge disposable tubes that served as electrotransformation cuvettes. A square-wave with pulse length set at 10 ms was applied using a custom-built pulse generator/titanium electrode system. A voltage threshold corresponding to the formation of electropores in a cell sample was evaluated as a non-linear current change when pulse voltage was linearly increased in 200V increments. A particular voltage that provided the best ratio of transformation yield versus cell viability rate at a given DNA concentration was used, which in this particular case was 25 kV/cm. Pulsed cells were initially diluted with 500 µl DSM 122 medium, held on ice for 10 minutes and then recovered at 55° C. for 4-6 hrs. Following recovery, cells transformed with pSGD9 were mixed with 2% agar medium containing kanamycin at 75 µg/ml and poured onto petri plates and incubated in anaerobic jars for 4 days. Cells transformed with pSGD8-Erm were allowed to recover at 48° C. for 4-6 hrs and were either plated in 2% agar medium at pH 6.0 containing erythromycin at 5 µg/ml or similar liquid media and incubated in anaerobic jars at 48° C. for 6 days. Either of the transformed cell lines may be used without further manipulation. However, an organism where elimination of expression of all genes that confer the ability to produce organic acids was obtained by performing a second (sequential) transformation. The second transformation was carried out as described above with the primary transformant substituted for the non-transformed cell suspension. The secondary transformant, ALK1, was grown on medium containing both kanamycin and erythromycin.

Sequencing of Knockout Regions

Sequencing of the site directed knockout regions was done by PCR from genomic DNA using Taq polymerase (New England Biolabs) and primers outside the regions of homologous overlap between the genome and the suicide vectors. Primers inside the PCR products were used for sequencing with the BigDye Terminator kit v3.1 (ABI, Foster City, Calif.). Regions were arranged using the CAP3 software program (Huang, X. "An improved sequence assembly program" Genomics 33: 21-31, 1996) and compared to the expected DNA sequence using the CLUSTALW algorithm (Higgins, D. G.; Bleasby, A. J.; Fuchs, R. "CLUSTAL V: improved software for multiple sequence alignment" Computer Applications in the Biosciences (CABIOS), 8(2): 189-191, 1992). A high degree of homology (percent identity) existed between the experimentally compiled sequence and the expected sequence based on the known wild-type and suicide vector sequences (FIGS. 3 and 4).

"Identity" refers to a comparison between pairs of nucleic acid or amino acid molecules. Methods for determining sequence identity are known. See, for example, computer programs commonly employed for this purpose, such as the Gap program (Wisconsin Sequence Analysis Package, Version 8 for Unix, Genetics Computer Group, University Research Park, Madison Wis.), that uses the algorithm of Smith and Waterman, 1981, Adv. Appl. Math. 2: 482-489.

Verification of Mutant Strain

Genomic DNA from the mutant strain Thermoanaerobacterium saccharolyticum JW/SL-YS485 ALK1 ("ALK1") showed the expected site-directed homologous recombination in the L-ldh and pta/ack loci through DNA sequencing. Both integration events were double integrations, which is a more genetically stable genotype.

Example 2

Comparative Data Showing Production of Ethanol by Alk1 and Wild-Type T. Saccharolyticum T. saccharolyticum was grown in partially defined MTC media containing 2.5 g/L Yeast Extract (Zhang, Y.; Lynd, L.

Figure 5:
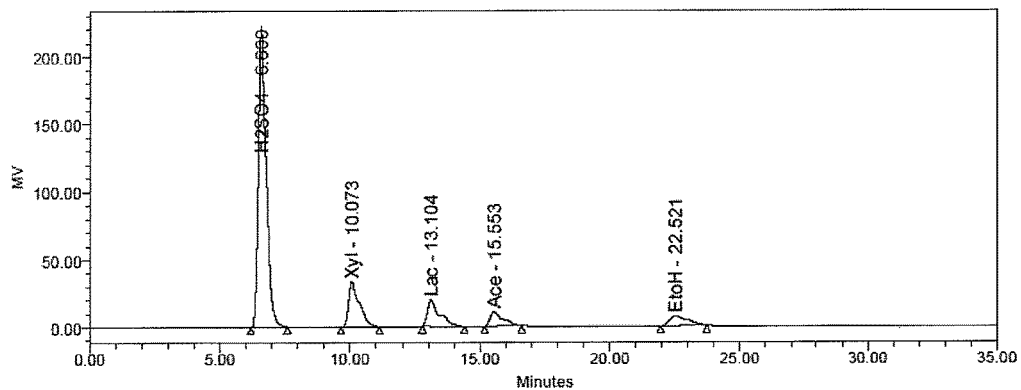
FIGS. 5-7 show high-performance liquid chromatography (HPLC) traces of a fermentation broth at various time intervals during growth of ALK1.

R. "Quantification of cell and cellulase mass concentrations during anaerobic cellulose fermentation: development of an enzyme-linked immunosorbent assay-based method with application to *Clostridium thermocellum* batch cultures" Anal. Chem. 75: 219-222, 2003). Glucose, xylose, acetate, lactate and ethanol were analyzed by HPLC on an Aminex 87H column (BioRad Laboratories, Hercules, Calif.) at 55° C. The mobile phase consisted of 5 mM sulfuric acid at a flow rate of 0.7 ml/min. Detection was via refractive index using a Waters 410 refractometer (Milford, Mass.). The minimum detection level for acetate was 1.0 mM. A standard trace containing 5 g/L xylose, 5 g/L lactic acid, 5 g/L acetic acid and 5 g/L ethanol is shown in FIG. 5.

Figure 6:
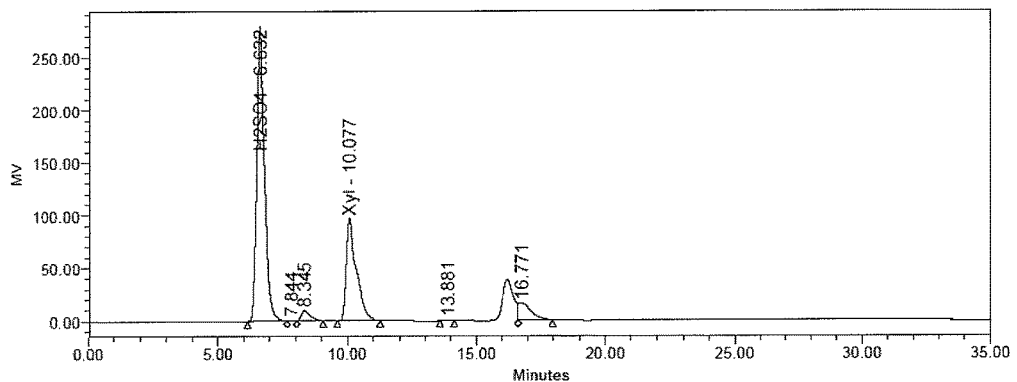
Figure 7:
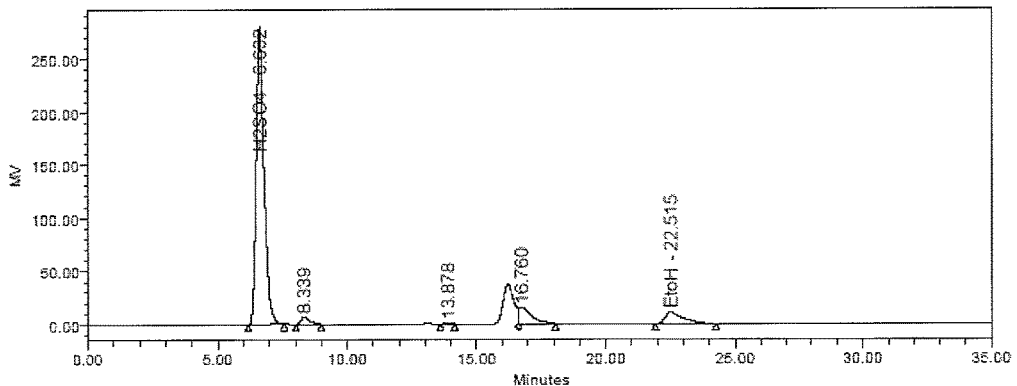
Figure 8:
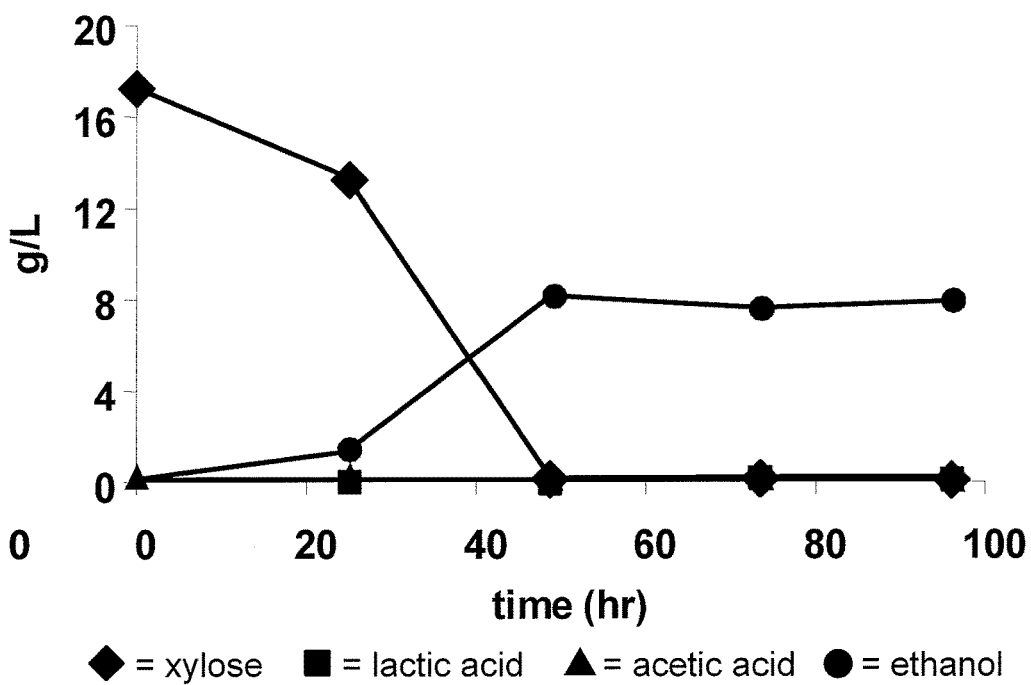
FIG. 8 shows xylose, organic acid and ethanol concentrations during fermentation by strain ALK1.
Figure 9:
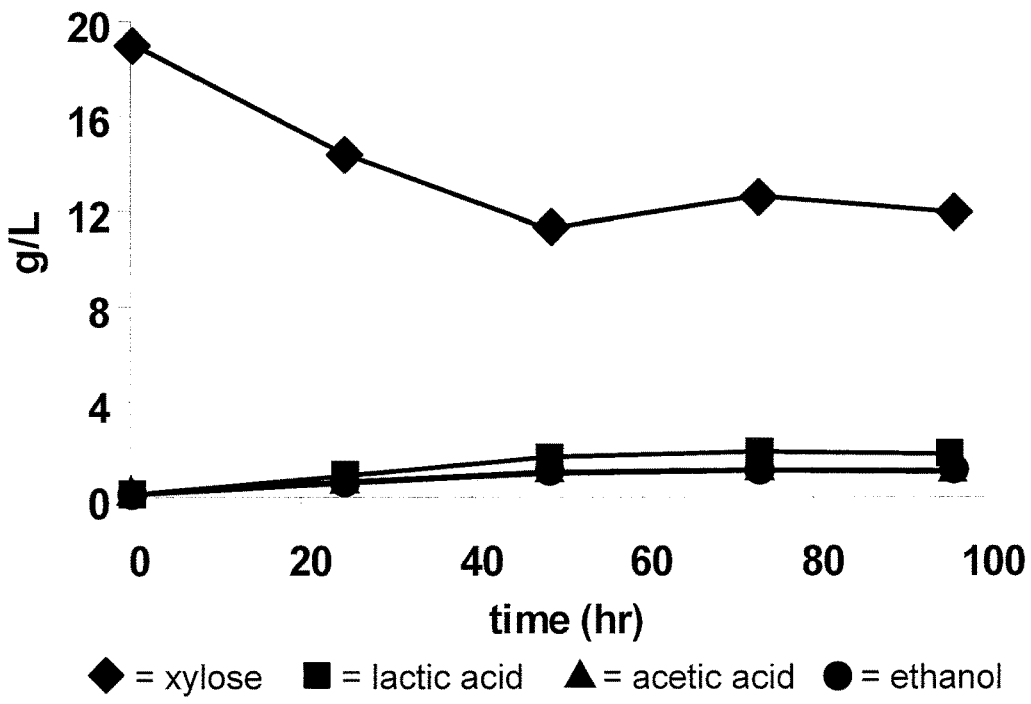
FIG. 9 shows xylose, organic acid and ethanol concentrations during fermentation by wild-type *T. saccharolyticum*.

Strain ALK1 produced only ethanol with up to 17 g/L xylose, or with 5 g/L xylose and 5 g/L glucose, with no organic acids or other products detected by HPLC. FIG. 6 shows the ALK1 strain fermentation at time 0 hours and FIG. 7 shows the same fermentation at 72 hours. Time course fermentation plots of strain ALK1 and wild-type on xylose media buffered with 8 g/L MES at an initial pH of 6.0, 55° C. and 100 rpm show that strain ALK1 is able to convert over 99% of xylose to ethanol (FIG. 8), while the wild-type under similar conditions becomes pH limited due to organic acid production and is unable to consume all the xylose present (FIG. 9). The wild-type organism yielded 0.15 mM ethanol, while ALK1 yielded 0.46 mM ethanol.

Example 3

Evolution of ALK1

Figure 10:
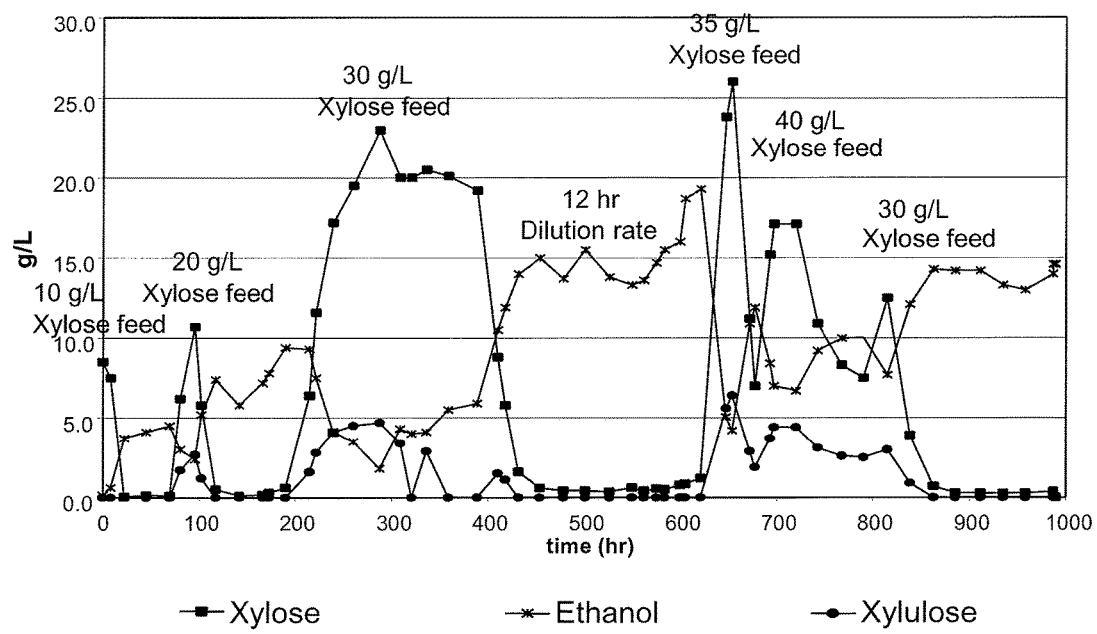
FIG. 10 shows xylose, organic acid and ethanol concentrations during a continuous culture challenge of ALK1.
Figure 11:
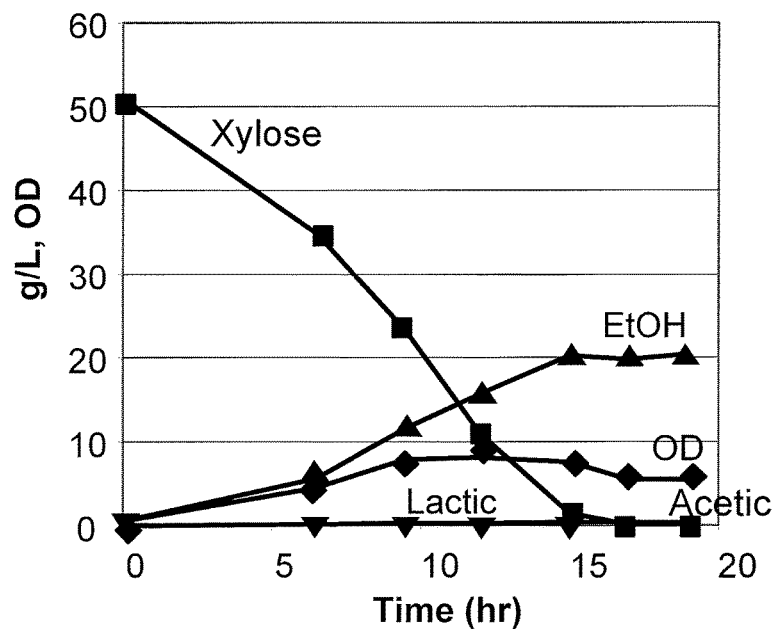
FIG. 11 shows xylose, organic acid and ethanol concentrations during fermentation by strain ALK2.

As shown in FIG. 10, a continuous culture in which feed substrate concentration was increased over time was utilized to challenge ALK1. FIG. 10 shows xylose, xylulose and ethanol concentrations during the continuous culture. After more than 1000 hours of exposure to this stress-evolution cycle, an improved strain, ALK2, was isolated from the fermentation broth. ALK2 was able to initiate growth at 50 g/L xylose in batch culture. FIG. 11 shows xylose, organic acid, optical density (OD) and ethanol concentrations during fermentation by strain ALK2.

Example 4

Thermophilic Simultaneous Saccharification and Fermentation

Some thermotolerant yeast strains have been tested for ethanol production via SSF at temperatures of 40-45° C., with reduced yield above these temperatures (Banat, I. M.; Nigam, P.; Singh, D.; Marchant, R.; McHale, A. P. "Review: Ethanol production at elevated temperatures and alcohol concentrations: Part I—Yeasts in general." *World Journal of Microbiology and Biotechnology* 14: 809-821, 1998). In addition, Patel et al. have demonstrated SSF at 50° C. for the production of lactic acid using a *Bacillus* strain (Patel, M. A.; Ou, M. S.; Ingram, L. O.; Shanmugam, K. T. "Simultaneous saccharification and co-fermentation of crystalline cellulose and sugar cane bagasse hemicellulose hydrolysate to lactate by a thermotolerant acidophilic *Bacillus* sp." *Biotechnol. Prog.* 21: 1453-1460, 2005). Thermophilic SSF has not, however, been previously demonstrated at 50° C. for the production of ethanol with reduced enzyme requirements.

As discussed above, thermophilic organisms transformed according to the present disclosure have the potential to contribute significant savings in lignocellulosic biomass to ethanol conversion due to their growth conditions, which are substantially optimal for cellulase activity in SSF processes. For example, ALK1 and ALK2 are anaerobic thermophiles that can grow at 50° C. and pH 5.0, while optimal cellulase activity parameters include a pH between 4-5 and temperature between 40-50° C.

Figure 12:
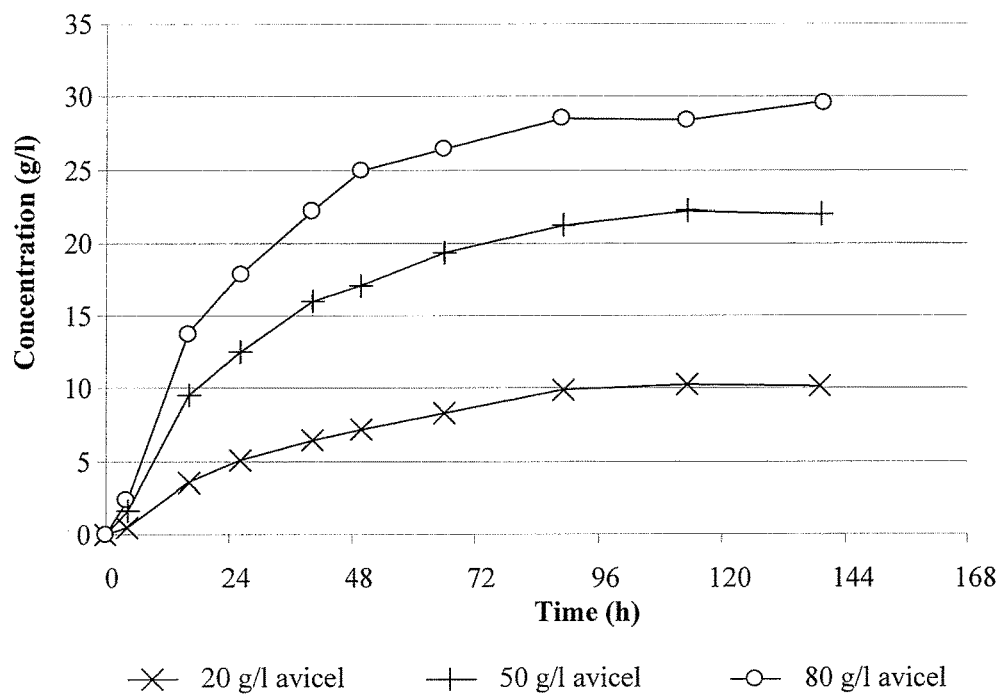
FIG. 12 shows ethanol production at various Avicel concentrations during thermophilic SSF reactions involving ALK2 and cellulase at 50° C.
Figure 13:
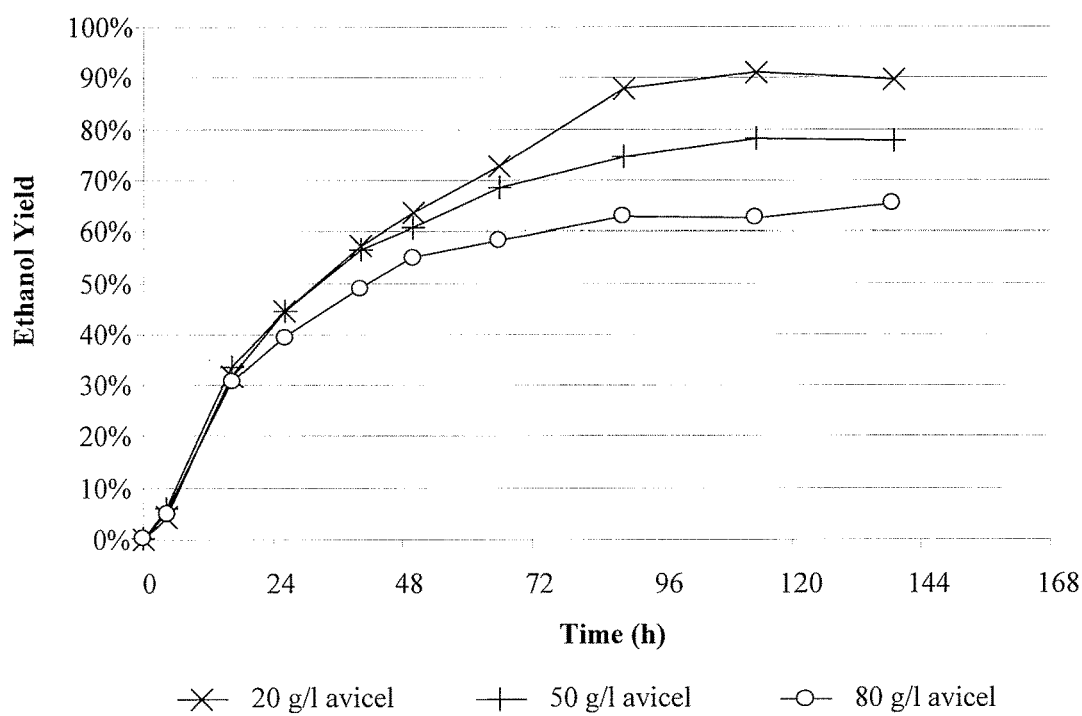
FIG. 13 shows ethanol yield for the thermophilic SSF reactions shown in FIG. 12.

In a thermophilic simultaneous saccharification and fermentation (tSSF) reaction performed on a 1.5 L scale in a batch reactor at 50° C., ALK2 was used in conjunction with 4 FPU/g *T. reesei* cellulase (Genencor, Palo Alto, Calif.) to produce ethanol from the solid substrate Avicel (20 g/L, 50 g/L and 80 g/L). There were no soluble sugars measured after sixteen hours of fermentation and less than 0.5 g/L lactic acid were produced in any of the trials. FIG. 12 shows that 30 g/L ethanol were produced in 140 hours when the tSSF reaction was performed on 80 g/l Avicel, with 25 of the 30 g/L ethanol produced in the first 50 hours. FIG. 13 shows ethanol yields for the reactions illustrated in FIG. 12. Yields were calculated based upon the theoretical maximum of 0.51 g ethanol per gram glucose equivalent. At 20 g/L Avicel, about 90% conversion was achieved in 140 hours.

It will be appreciated that *T. saccharolyticum* can ferment both pentose and hexose sugars. The disclosed organisms can therefore be used in Simultaneous Saccharification and Co-Fermentation (SSCF) reactions, where an enzyme that converts hemicellulose into pentose sugars (e.g., xylase) may be utilized in combination with cellulase.

Deposit of ALK1

ALK1 has been deposited with the American Type Culture Collection, Manassas, Va. 20110-2209. The deposit was made on Nov. 1, 2005 and received Patent Deposit Designation Number PTA-7206. This deposit was made in compliance with the Budapest Treaty requirements that the duration of the deposit should be for thirty (30) years from the date of deposit or for five (5) years after the last request for the deposit at the depository or for the enforceable life of a U.S. patent that matures from this application, whichever is longer. ALK1 will be replenished should it become non-viable at the depository.

The description of the specific embodiments reveals general concepts that others can modify and/or adapt for various applications or uses that do not depart from the general concepts. Therefore, such adaptations and modifications should and are intended to be comprehended within the meaning and range of equivalents of the disclosed embodiments. It is to be understood that the phraseology or terminology employed herein is for the purpose of description and not limitation.

The foregoing examples may be suitably modified for use upon any Gram-positive bacterium, and especially members of the *Thermoanaerobacter* genus including *Thermoanaerobacterium thermosulfurigenes*, *Thermoanaerobacterium aotearoense*, *Thermoanaerobacterium polysaccharolyticum*, *Thermoanaerobacterium zeae*, *Thermoanaerobacterium thermosaccharolyticum*, and *Thermoanaerobacterium xylanolyticum*.

All references mentioned in this application are incorporated by reference to the same extent as though fully replicated herein.

What is claimed is:

1. An engineered Gram-positive bacterium that ferments a saccharification product of a cellulolytic substrate to produce ethanol, wherein said bacterium converts pyruvate to acetyl-CoA by means of pyruvate-ferredoxin oxidoreductase, and wherein at least three genes in said bacterium have been disrupted through homologous recombination, said three genes being ldh gene, phosphotransacetylase (pta) gene and acetate kinase (ack) gene, wherein said bacterium has an ethanol yield at least 90% of theoretical yield.

2. A method for producing ethanol, said method comprising:
   transforming a native bacterium to produce the engineered bacterium of claim 1; and
   culturing the engineered Gram-positive bacterium in a medium that contains a substrate including a material selected from the group consisting of glucose, xylose, mannose, arabinose, galactose, fructose, cellobiose, sucrose, maltose, xylan, mannan, starch, and combinations thereof under suitable conditions for a period of time sufficient to allow saccharification and fermentation of the substrate to produce ethanol.

3. The bacterium of claim 1, wherein said Gram-positive bacterium belongs to the genus selected from the group consisting of the *Thermoanaerobacterium* genus and the *Thermoanaerobacter* genus.

4. The bacterium of claim 1, wherein said bacterium is a *Thermoanaerobacterium saccharolyticum*.

5. The bacterium of claim 1, wherein said bacterium is designated ALK1 and deposited under Patent Deposit Designation No. PTA-7206.

6. A biologically pure culture of a microorganism designated ALK1 and deposited under Patent Deposit Designation No. PTA-7206.

7. A genetic construct designated pSGD9 comprising a polynucleotide having a sequence at least 99% identical to:
   (a) the sequence of SEQ ID NO: 10; or
   (b) the sequence of SEQ ID NO: 9.

8. The genetic construct of claim 7, wherein the polynucleotide comprises a sequence 100% identical to the sequence of (a) or (b).

9. A vector comprising the genetic construct of claim 7.

10. A host cell genetically engineered to express the vector of claim 9.

11. The host cell of claim 10, wherein the host cell is a bacterial cell.

12. A method of producing ethanol, comprising the step of: culturing the engineered Gram-positive bacterium of claim 1 in a medium containing a substrate selected from the group consisting of glucose, xylose, mannose, arabinose, galactose, fructose, cellobiose, sucrose, maltose, xylan, mannan, starch, and combinations thereof under suitable conditions for a period of time sufficient to allow saccharification and fermentation of the substrate to produce ethanol.

13. The method of claim 12, wherein the engineered Gram-positive bacterium is *Thermoanaerobacterium saccharolyticum*.

14. The method of claim 13, wherein the engineered Gram-positive bacterium is *Thermoanaerobacterium saccharolyticum* ALK1 (JW/SL-YS485 ALK1).

15. A recombinant bacterium comprising the genetic construct of claim 7.

16. The recombinant bacterium of claim 15, wherein said bacterium is *Thermoanaerobacterium saccharolyticum*.

17. A method for producing ethanol, said method comprising:
   providing within a reaction vessel, a reaction mixture comprising lignocellulosic substrate, cellulase and a fermentation agent, the fermentation agent comprising the engineered Gram-positive bacterium of claim 1,
   wherein the reaction mixture is reacted under suitable conditions for a period of time sufficient to allow saccharification and fermentation of the lignocellulosic substrate to produce ethanol.

18. The method of claim 17, wherein the suitable conditions comprise a temperature of at least 50° C.

19. The method of claim 17, wherein the Gram-positive bacterium is a member of the *Thermoanaerobacter* genus.

20. The method of claim 17, wherein the Gram-positive bacterium is a *Thermoanaerobacterium saccharolyticum*.

* * * * *